US011518791B2

(12) United States Patent
Dervillez et al.

(10) Patent No.: US 11,518,791 B2
(45) Date of Patent: Dec. 6, 2022

(54) MULTIFUNCTIONAL HETEROMULTIMERIC CONSTRUCTS

(71) Applicants: Luxembourg Institute of Health (LIH), Luxembourg (LU); Université de Reims Champagne Ardenne URCA, Reims (FR)

(72) Inventors: Xavier Dervillez, Prümzurlay (DE); Carole Devaux, Zoufftgen (FR); Jacques H. M. Cohen, Reims (FR)

(73) Assignees: Luxembourg Institute of Health (LIH), Luxembourg (LU); Université de Reims Champagne Ardenne URCA, Reims (FR)

( * ) Notice: Subject to any disclaimer, the term of this patent is extended or adjusted under 35 U.S.C. 154(b) by 577 days.

(21) Appl. No.: 16/303,406

(22) PCT Filed: May 22, 2017

(86) PCT No.: PCT/EP2017/062283
§ 371 (c)(1),
(2) Date: Nov. 20, 2018

(87) PCT Pub. No.: WO2017/202776
PCT Pub. Date: Nov. 30, 2017

(65) Prior Publication Data
US 2019/0382458 A1 Dec. 19, 2019

(30) Foreign Application Priority Data
May 23, 2016 (LU) ........................................ 93082

(51) Int. Cl.
| C07K 14/47 | (2006.01) |
| C07K 16/30 | (2006.01) |
| C12N 15/62 | (2006.01) |
| C07K 14/475 | (2006.01) |
| C07K 14/52 | (2006.01) |
| C07K 14/705 | (2006.01) |
| C07K 16/18 | (2006.01) |
| C07K 19/00 | (2006.01) |
| C07K 14/745 | (2006.01) |

(52) U.S. Cl.
CPC .......... *C07K 14/472* (2013.01); *C07K 14/475* (2013.01); *C07K 14/52* (2013.01); *C07K 14/705* (2013.01); *C07K 14/745* (2013.01); *C07K 16/18* (2013.01); *C07K 16/30* (2013.01); *C07K 19/00* (2013.01); *C12N 15/62* (2013.01); *C07K 2317/732* (2013.01); *C07K 2317/734* (2013.01); *C07K 2318/20* (2013.01); *C07K 2319/035* (2013.01); *C07K 2319/30* (2013.01); *C07K 2319/32* (2013.01); *C07K 2319/60* (2013.01); *C07K 2319/61* (2013.01); *C07K 2319/735* (2013.01); *C07K 2319/74* (2013.01)

(58) Field of Classification Search
CPC .. A61K 38/1709; A61K 47/60; A61K 38/177; A61K 9/1272; A61K 48/0033; A61K 45/06; A61P 43/00; A61P 7/04; C07K 14/47; C07K 14/70596; C12N 2320/32; G01N 33/574; G01N 33/6854
See application file for complete search history.

(56) References Cited

FOREIGN PATENT DOCUMENTS

| EP | 2298898 A1 | 3/2011 |
| EP | 1 951 313 B1 * | 1/2015 |
| WO | WO 00/69907 A1 | 11/2000 |
| WO | WO 2004/016283 A2 | 2/2004 |
| WO | WO 2004/020639 A2 | 3/2004 |
| WO | WO 2008/106644 A2 | 9/2008 |

OTHER PUBLICATIONS

Ashby et al, TRENDS in Neurosciences, 2004; vol. 27 No. 5, pp. 257-261.*
Devaux et al, Molecular Oncology ; 2019; vol. 13, pp. 2531-2553.*
Ogun et al, Infection and Immunity, 2008, vol. 76, No. 8, pp. 3817-3823.*
Dervillez et al, ChemMedChem; 2006, vol. 1, pp. 330-339.*
Tokuriki and Tawflik, Current Opinion in Structural Biology 2009, 19: 596-604.*
Fenton et al. 2020, Medicinal Chemistry Research 29:1133-1146.*
Bhattacharya et al. (2017, PLoS ONE 12(3): e0171355.*
Alaoui-Ismaili; 2009, Cytokine Growth Factor Rev. 20(5-6):501-507) .*
Guo et al. (2004, PNAS USA 101(25):9205-10.*
Christiansen et al., "Octamerization Enables Soluble CD46 Receptor to Neutralize Measles Virus In Vitro and In Vivo," *J. of Virology*, 74(10): 4672-4678 (May 1, 2000). Oudin et al., "A Soluble Recombinant Multimeric Anti-Rh (D) Single-Chain Fv/CR1 Molecule Restores the Immune Complex Binding Ability of CR1-Deficient Erythrocytes," *J. of Immunology*, 164(3): 1505-1513 (Feb. 1, 2000).
Zahn-Zabal et al., "Development of stable cell lines for production or regulated expression using matrix attachment regions," *J. of Biotechnology*, 87(1): 29-42 (Apr. 27, 2001).
European Patent Office, International Search Report in International Patent Application No. PCT/EP2017/062283, 6 pp. (dated Jul. 19, 2017).

(Continued)

*Primary Examiner* — Bridget E Bunner
*Assistant Examiner* — Fozia M Hamud
(74) *Attorney, Agent, or Firm* — Leydig, Voit & Mayer, Ltd.

(57) ABSTRACT

The present invention is situated in the field of multimers used for targeted therapies. More particularly, the invention relates to methods for preparing multifunctional heteromultimeric protein complexes with a defined ratio of functional components and to multifunctional heteromultimeric protein complexes for directing complement-dependent cytolysis, optionally comprising a scaffold, which display three or more different functional components present in a defined relative ratio, of which one is a tracking component.

11 Claims, 13 Drawing Sheets

(56) References Cited

OTHER PUBLICATIONS

European Patent Office, Written Opinion in International Patent Application No. PCT/EP2017/062283, 7 pp. (dated Jul. 19, 2017).

* cited by examiner a) Step 1 (TaF), 2A (EF), 2B (EF)

b) Step 1 c) Step 1 d) Step 2B a)

b)

MULTIFUNCTIONAL HETEROMULTIMERIC CONSTRUCTS

CROSS-REFERENCE TO RELATED APPLICATIONS

This patent application is a U.S. National Phase application of International Patent Application No. PCT/EP2017/062283, filed May 22, 2017, which claims the benefit of Luxembourg Patent Application No. LU93082, filed May 23, 2016, each which is incorporated herein by reference in its entirety.

TECHNICAL FIELD

The present invention is situated in the field of multimers used for targeted therapies. More particularly, the invention relates to multifunctional multimers, optionally comprising a scaffold, which display two or more different functional components.

BACKGROUND OF THE INVENTION

Multimeric systems offer the opportunity to combine several functional components, such as components with a therapeutic and a targeting functionality, into one molecule, allowing targeted therapy which often increases effectiveness and reduces unwanted side-effects. Joint delivery of different therapeutic components can lead to a synergistic therapeutic effect. In addition or alternatively, the combination of different targeting components may increase the binding specificity and affinity.

In most cases, the functional components are attached to a scaffold or backbone composed of, for example, dendrimers, antibodies and poly lysine. Although highly efficient, these multimeric systems have some drawbacks. First, their chemical formulation is not precisely defined. Second, the number of functional components being added to a polymer molecule is often random and cannot be controlled. This is particularly troublesome when it is of interest to load a combination of functional components on such a polymer. An example is given below.

The main actor of the innate immunity is the complement system, acting as a fast and efficient immune surveillance system able to discriminate among healthy host tissue, cellular debris, apoptotic cells and foreign intruders by promoting inflammation through the modification of the status of the target membrane surfaces that become the siege and focus of opsonisation by the central C3 complement component. Subsequent events of the complement-directed inflammatory cascade lead to the generation of C3- and C5-convertases that orchestrate the assembly of the membrane attack complexes C5b-9 (MAC), leading to direct cell killing. Complement-mediated tumour cell killing is not the principal cytotoxic mechanism, while C3b degradation products (e.g. iC3b, C3d,g, C3d) on opsonised tumour targets are ligands for complement CR3, CR4 complement receptors on host phagocytic cells (e.g. macrophages, neutrophils, NKs, mast cells). Furthermore, anaphylatoxins (C3a, C5a) released from the generation of C3-105-convertases attract towards the sites of opsonisation further host immune cells of the adaptive immunity, thus reinforcing the host immune response towards opsonised tumour cells.

Directing complement activation exclusively towards unwanted cells to promote a host destructive cell targeting is thus an attractive strategy.

The first therapeutic application involving complement activation was the development of monoclonal antibodies in cancer therapy, aiming at promoting antibody-dependent cell-mediated cytotoxicity (ADCC) and complement-dependent cytotoxicity (CDC) of tumor cells. However, the focus of the therapeutic effect of most of these antibodies lies mainly on eliciting ADCC. The contribution of CDC in the therapeutic potency of mAbs remains controversial, with some exceptions such as anti-CD20 mAbs Rituximab (RTX) and Ofatumumab (OFA) activating the complement classical pathway (CCP) which is regulated by C4b binding protein (C4bp) and C1-inhibitor further merging to the C3b amplification loop.

In 2000, Vuagnat et al. showed that a membrane-anchored version of the human Properdin factor expressed on HEK293 cells, was able to promote the C3b assembly on Properdin-expressing cells (1), although direct lysis was less than 10% of PI-positive cells. Spitzer et al. generated a fusion protein combining an anti-human glycophorin A (GYPA) scFv and human Properdin and demonstrated that the fusion molecules bound human erythrocytes and triggered C3b deposition in the presence of autologous serum, but not to levels leading to the lysis of erythrocytes (2). They concluded that the presence of CD59 prevented the formation of MACs. Thus, monovalent bifunctional fusion proteins directing CDC on erythrocytes, were unable to lyse erythrocytes.

EP1951313 B1 describes the use of protein constructs for targeting and lysis of cells. More specifically, it describes heteromultimeric molecules comprising anti-GYPA scFv to target erythrocytes or anti-carcinoembryonic antigen (CEA) $V_HH$ to target certain tumor cells and fragment C of Tetanus toxin (TTfC) as an effector component. The use of TTfC-C4bpα/anti-GYPA scFv.C4bpα multimers directed against erythrocytes resulted in a partial cytolysis of the erythrocytes. After transfection and expression of TTfC-C4bpα/anti-GYPA scFv.C4bpα protein constructs in 293T cells, multimers with a variable valence were secreted. The main disadvantage of such uncontrollable valence is that the success of binding the target cell and recruiting the complement is mostly dependent on luck, which results in low reproducibility.

In view of the above, there remains a pressing need for an improved method for preparing multifunctional heteromultimers so that the number of functional components within the multimers can be better controlled.

SUMMARY

The present invention provides methods for preparing multifunctional heteromultimeric protein complexes with a defined ratio of functional components. Indeed, the inventors have developed methods to ensure that multimers with a defined number of each of the functional components can be obtained.

In one aspect the invention provides methods for preparing multifunctional heteromultimeric protein complexes with a defined ratio of functional components, which comprise two or more subsequent or transfections with a sequence encoding a multimerizing scaffold polypeptide fused to a tracking component and one or more sequences encoding multimerizing scaffold polypeptides fused to a functional component and determining the ratio of said one or more functional components to said tracking component. In particular embodiments, the methods comprise the steps of: (a) co-transfecting host cells with a nucleic acid vector that encodes a tracking component fused to a first multimerizing scaffold polypeptide, and with a nucleic acid vector that encodes a second functional component different from said tracking component fused to a second multimerizing scaffold polypeptide; (b) expressing the multimerizing scaffold peptides and allowing them to multimerize into bifunctional multimers, comprising a fixed number of one or more tracking components and said second functional component; (c) selecting the single-cell clones that secrete the bifunctional multimers; (d) transfecting said clones with a nucleic acid vector that encodes a third functional component different from said tracking component and said second functional component, fused to a third multimerizing scaffold polypeptide and optionally simultaneously or subsequently with a nucleic acid vector that encodes a fourth functional component different from said tracking component and from said second and third functional component fused to a fourth multimerizing scaffold polypeptide; (e) expressing the multimerizing scaffold polypeptides and allowing them to multimerize into multimers comprising a fixed number of one or more tracking components and one or more of said second and third and optionally one or more of said fourth functional component; (f) selecting single-cell clones secreting multimers having the desired relative ratio of second, third and optionally fourth functional components; and (g) recovering from said clones the produced multimeric protein complexes.

In particular embodiments, said methods comprise the simultaneous or subsequent transfection with not only a fourth but (X-4) additional nucleic acid vectors that encode a further functional component different from said tracking component and said other functional components fused to a multimerizing scaffold polypeptides, wherein said multimers can comprise X functional components, and wherein X is a natural number between 4 and 20 and is at most the total number of polypeptides present in the multimerizing scaffold.

In particular embodiments, said selection step comprises tagging each of said second, third and optionally up to $X^{th}$ functional components or each of said second, third and optionally up to $X^{th}$ multimerizing scaffold polypeptides and determining the expression of each of said components or of each of said polypeptides relative to said tracking component or said first multimerizing polypeptide by said host cell, wherein X is a natural number between 4 and 20 and is at most the total number of polypeptides present in the multimerizing scaffold.

In particular embodiments, said methods comprise, after step (c) and in replacement of steps (d) to (f), the steps of (i) transfecting said clones with a nucleic acid vector that encodes a third functional component fused to a third multimerizing scaffold polypeptide; (ii) expressing multimerizing polypeptides and allowing them to multimerize into multimers comprising a fixed number of one or more of said tracking components and comprising one or more of said second and third functional components; (iii) selecting single-cell clones secreting multimers having the desired relative ratio of second and third functional components; (iv) transfecting said clones with a nucleic acid vector that encodes a fourth functional component fused to a fourth multimerizing scaffold polypeptide; (v) expressing the multimerizing polypeptides and allowing them to multimerize into multimers comprising a fixed number of one or more tracking components and one or more of said second, third and fourth functional component; (vi) selecting single-cell clones secreting multimers having the desired relative ratio of second, third and fourth functional components; (vii) optionally, repeating said steps of transfecting, expressing, and selecting for the complexes comprising said (X-4) functional components each fused to a multimerizing scaffold polypeptide, wherein the X is a natural number between 4 and 20 and is at most the total number of polypeptides present in the multimerizing scaffold.

In particular embodiments, said nucleic acid vector is a multi-cistronic expression vector encoding two or more functional components each fused to a multimerizing scaffold polypeptide. In particular embodiments, said functional components comprise one or more targeting components and one or more effector components. In particular embodiments, at least one, preferably at least two, of the functional components is a monomeric Fc. In particular embodiments, at least one of the effector components is a factor capable of modulating the complement system, preferably wherein at least one of the effector components is factor H-related protein 4 (FHR4) or Properdin factor, more preferably wherein at least one of the effector components is FHR4. In particular embodiments, at least one of the targeting components is selected from the group consisting of antibodies, binding fragments thereof, ligands to a target cell receptor, and soluble receptors, preferably wherein at least one of the targeting components is an antibody or a binding fragment thereof directed against a tumor antigen, against a surface marker of erythrocytes or against a pathogen-associated surface marker, more preferably wherein at least one of the targeting components is multi-2D3 $V_HH$ anti-HER2 or scFv anti-GYPA. In particular embodiments, the relative ratio of tracking and second and third functional components is 1:N:M, wherein N represents the second functional component and M represents the third functional component and wherein N+M equals 7. In particular embodiments, said multimerizing scaffold polypeptides are components of a C4bp protein. In particular embodiments, said tracking component is fused to the beta-chain of C4bp, preferably to the c-terminal part of a beta-chain of C4bp. In particular embodiments, each alpha-chain of C4bp is fused to two functional components. In particular embodiments, a first functional component is located upstream and a second functional component is located downstream of the alpha-chain of C4pb. In particular embodiments, one of the functional components fused to the alpha-chain of C4pb is monomeric Fc.

A further aspect of the invention provides multifunctional heteromultimeric protein complexes for directing complement-dependent cytolysis and/or antibody-dependent cell-mediated cytotoxicity, comprising three or more different functional components present in a defined relative ratio, of which one is a tracking component.

In particular embodiments, said multifunctional heteromultimeric protein complexes comprise at least four different functional components. In particular embodiments, each functional component is fused to a multimerizing scaffold polypeptide. In particular embodiments, said multifunctional heteromultimeric protein complexes comprise one or more targeting components and one or more effector components. In particular embodiments, the functional components are selected from the group comprising synthetic or natural peptides, biological macromolecules, polypeptides, proteins, peptide analogues, peptide-mimetics, antibodies, antibody fragments and derivatives thereof. In particular embodiments, said targeting component is selected from the group consisting of protein-based binding molecules, such as antibodies, binding fragments thereof, ligands to a target cell receptor, and soluble receptors, preferably wherein at least one of the targeting components is an antibody, a binding fragment thereof or a cell-surface receptor ligand, more preferably wherein at least one of the targeting components is an antibody or a binding fragment thereof directed against a tumor antigen, against a surface marker of erythrocytes or against a pathogen-associated surface marker, even more preferably wherein at least one of the targeting components is multi-2D3 $V_HH$ anti-HER2 or scFv anti-GYPA. In particular embodiments, at least one of the effector components is a factor capable of modulating the complement system, preferably wherein at least one of the effector components is FHR4 or Properdin, more preferably wherein at least one of the effector components is FHR4. In particular embodiments, said tracking component is selected form the group consisting of fluorescent dyes, magnetic beads, biotin for staining with labelled avidin or streptavidin conjugate, enzymes, substrates, cofactors, chemiluminescent groups, chromogenic agents, colorimetric labels and beads. In particular embodiments, said multimerizing scaffold polypeptides comprise at least two monomeric Fc. In particular embodiments, said multimerizing scaffold polypeptides comprise at least 3, preferably at least 6 FHR4 proteins. In particular embodiments, said multimerizing scaffold polypeptides are components of the C4bp protein. In particular embodiments, the tracking component is fused to the beta-chain of C4bp, preferably to the c-terminal part of a beta-chain of C4bp. In particular embodiments, each alpha-chain of C4bp is fused to two functional components. In particular embodiments, a first functional component is located upstream and a second functional component is located downstream of the alpha-chain of C4pb. In particular embodiments, one of the functional components fused to the alpha-chain of C4pb is monomeric Fc.

A further aspect of the invention relates to the multifunctional heteromultimeric protein complexes as envisaged herein for use as a medicament. In particular embodiments, said multifunctional heteromultimeric protein complexes are used in medical applications such as drug delivery, cell removal, cell targeting, cancer therapy, immunotherapy and medical imaging. In particular embodiments, said multifunctional heteromultimeric protein complexes are used in immunotherapy.

A further aspect of the invention relates to the multifunctional heteromultimeric protein complexes as envisaged herein for use in the treatment of cancer, preferably breast cancer, more preferably HER2-positive breast cancer.

A further aspect of the invention relates to a method of treating a patient suffering from cancer comprising administering to said subject a therapeutically effective amount of the multifunctional heteromultimeric complex as envisaged herein.

A further aspect of the invention relates to the multifunctional heteromultimeric protein complexes as envisaged herein for use in the treatment of an autoimmune disease or infectious disease involving an intracellular microorganism, preferably said infectious disease involving an intracellular microorganism is selected from tuberculosis, gonorrhea infection, cystic fibrosis, *Borrelia* infection, *Plasmodium falciparum* infection, Haemophilius infection, *Staphylococcus* infection, *Salmonella* infection, *Yersinia* infection, influenza, measles, hepatitis B, hepatitis C, HIV, leptospirosis, Lemierre's syndrome and meningitis and other forms of meningococcal disease, and infections caused by multi drug resistant bacteria, more preferably said infectious disease involving an intracellular microorganism is HIV.

A further aspect of the invention provides a method of treating a patient suffering from an autoimmune disease or infectious disease involving an intracellular microorganism comprising administering to said subject a therapeutically effective amount of a multifunctional heteromultimeric complex as described herein, wherein said infectious disease involving an intracellular microorganism is preferably selected from tuberculosis, gonorrhea infection, cystic fibrosis, *Borrelia* infection, *Plasmodium falciparum* infection, Haemophilius infection, *Staphylococcus* infection, *Salmonella* infection, *Yersinia* infection, influenza, measles, hepatitis B, hepatitis C, HIV, leptospirosis, Lemierre's syndrome and meningitis and other forms of meningococcal disease, and infections caused by multi drug resistant bacteria, more preferably wherein said infectious disease involving an intracellular microorganism is HIV. A further aspect of the invention provides pharmaceutical compositions comprising the multifunctional heteromultimeric protein complexes according to the invention and a pharmaceutically acceptable carrier.

BRIEF DESCRIPTION OF THE FIGURES

The following description of the figures of specific embodiments of the invention is merely exemplary in nature and is not intended to limit the present teachings, their application or uses.

Step 1: Generation of the α-β bifunctional heteromultimers. Co-transfection of HEK293 cells with TaF and TrF plasmids to generate 7α-1β bifunctional heteromultimers such as (i) multi-scFv anti-GYPA.C4bpα.FLAG/mono-eGFP.C4bpβ to target human erythrocytes, or (ii) multi-2D3 $V_HH$ anti-Her2.C4bpα.FLAG/mono-eGFP.C4bpβ to target Her2-expressing tumour cells. This step includes (i) an antibiotic selection (e.g., puromycin), (ii) a subcloning and (iii) a screening to identify a clone expressing high amounts of bifunctional heteromultimers.

Step 2A: Generation of the α-β trifunctional heteromultimers. A selected cell clone expressing the bifunctional heteromultimers from Step 1 was co-transfected with EF and pTK-Hygro plasmids to generate the following trifunctional heteromultimers:

For erythrocyte targeting:
multi-Properdin.C4bpα.His/multi-scFv anti-GYPA.C4bpα.FLAG/mono-eGFP.C4bpβ
multi-FHR4.C4bpα.His/multi-scFv anti-GYPA.C4bpα.FLAG/mono-eGFP.C4bpβ.

For Her2-expressing tumour cell Targeting:
multi-FHR4.C4bpα.His/multi-2D3 $V_HH$ anti-Her2.C4bpα.FLAG/mono-eGFP.C4bpβ.

This step includes (i) an antibiotic selection (e.g., puromycin+hygromycin), (ii) a subcloning and (iii) a screening to identify a clone expressing trifunctional heteromultimers with low EF or high EF valences.

Step 2B: Generation of the α-α-α-β tetrafunctional heteromultimers. A selected cell clone expressing the bifunctional heteromultimers from Step 1 was co-transfection with FHR4 and Properdin EF and pTK-Hygro plasmids to generate the following tetrafunctional heteromultimers:

Target erythrocytes:
multi-Properdin.C4bpα.His/multi-FHR4.C4bpα.His/multi-scFv anti-GYPA.C4bpα.FLAG/mono-eGFP.C4bpβ

Target Her2-expressing tumour cells:
multi-Properdin.C4bpα.His/multi-FHR4.C4bpα.His/multi-$V_HH$ anti-Her2.C4bpα.FLAG/mono-eGFP.C4bpβ.

This step includes (i) an antibiotic selection (e.g., puromycin+hygromycin), (ii) a subcloning and (iii) a screening to identify a clone expressing tetrafunctional heteromultimers with high EF valences and optimized FHR4/Properdin ratios.

FIG. 2: Expression cassettes for effector, targeting, and tracking functions.

a) Expression cassette for effector (EF) or targeting functions (TaF). P: Promoter (e.g. SV40 or human polypeptide chain elongation factor 1α); SP: Signal peptide (e.g. low-affinity nervous growth factor receptor, LNGFR); EF: Effector function (e.g. P: Properdin, F: FHR4); TaF: Targeting function (e.g. scFv, $V_HH$, soluble receptor, ligand); L: SG4S linker (from about 1 to up to about 15 repeats); MS: C-terminal multimerising scaffold of the C4bp α-chain; T: Tag (e.g. His, FLAG, HA, c-myc) for ELISA, FACS and/or purification b) Expression cassette for the tracking function (TrF). SP: Signal peptide; TrF: Tracking function (e.g. eGFP, luciferase). L: SG4S linker (1 to up to 15); SCR3: Third consensus repeat of the C4bp β-chain. C4bp 3: C-terminal fragment of the C4bp β-chain.

c) Co-expression of TaF and TrF functions in Step 1 of FIG. 1 can be performed via a unique bi-cistronic vector for stable expression of recombinant functional components in mammalian cells. The vector can then display 2 distinct promoters, each one driving the translation of a single gene.

d) Co-expression of 2 EF depicted in Step 2B of FIG. 1 can be realized in a unique bi-cistronic vector. As in FIG. 2*c*, each EF can be driven by an individual promoter, or by a single promoter upstream from the first EF gene, followed by an IRES allowing the translation of the second EF gene.

FIG. 3: Screening of trifunctional heteromultimers for low and high effector valences (FHR4 or Properdin) in an erythrocyte target model.

Properdin or FHR4 valences of secreted trifunctional heteromultimers were determined for isolated cell clones according to the ratios MFI Properdin/MFI eGFP or MFI FHR4/MFI eGFP measured by flow cytometry on multimer-loaded erythrocytes. CAP-effector valence ranges from 1 to 6. a) Properdin-based trifunctional heteromultimers: Ratios MFI Properdin/eGFP of trifunctional multimer-containing supernatants from 8 clones were calculated and distributed from the lowest to the highest ratios over a scale spanned from 1 to 6. PL and PH are the trifunctional multimers with lowest and the highest Properdin valences, respectively. b) The same calculation has been made for the FHR4-based trifunctional heteromultimers from 8 clones. FL and FH are the trifunctional multimers with the lowest and highest FHR4 valences, respectively. The bulk corresponds to the intermediate FHR4 valences.

FIG. 4: Relationship between PRCAP valence within multimers, opsonisation and hemolysis efficacy in the erythrocyte target model. Trifunctional multimers: PL: Properdin low; PH: Properdin high; FL: FHR4 low; FH: FHR4 high; Tetrafunctional multimer: FP: FHR4/Properdin; Bifunctional control multimer: A: multi-scFv glycophorin A/mono-eGFP. a) Comparative C3b deposition on human erythrocytes ($A^+$) loaded with 6 distinct multimers in veronal buffer supplemented with C5-deficient $A^+$ serum. Erythrocytes were then stained with anti-C3b mouse anti-human C3b mAb and analysed by FACS. b) Lysis of erythrocytes loaded with the 6 distinct multimers and incubated with autologous NHS. c) Factor H-mediated dose-response inhibition of opsonisation of FHR4-loaded erythrocytes. Effect of multimers according to an embodiment of the invention on erythrocytes. Analysis by flow cytometry of the dose-response inhibition of C3b-assembly by soluble factor H on trifunctional high FHR4-valence heteromultimer-loaded erythrocytes. Erythrocytes ($A^+$) were incubated with (i) about 100 nMoL of trifunctional high FHR4 valence heteromultimers in veronal buffer containing ABO-compatible serum from a C5-deficient donor and with (ii) serial dilutions of soluble factor H. MFI for C3b-assembly was measured by FACS. Constant MFI for eGFP shows equal multimer densities on erythrocytes for each FH concentration.

Statistics: Two-tailed unpaired t test. $p \geq 0.05$; *: $p<0.05$; : $p<0.01$; *: $p<0.001$, for triplicate experiments.

FIG. 5: Analysis by flow cytometry of the ability of the 2D3 $V_HH$ anti-Her2/eGFP bifunctional heteromultimer to bind to Her2-overexpressing breast tumor cell lines.

a) Comparative determination of the relative Her2-expression on 3 Her2 overexpressing tumour cell lines. BT474, SK-BR-3, SK-OV-3 and control HEK293 cells were stained with Trastuzumab and then an anti-human IgG Ab conjugated with a APC. b) Analysis of the in vitro dose-response binding of the bifunctional heteromultimers on BT474 vs. SK-BR-3 target cells. Serial dilutions of the bifunctional heteromultimer-containing crude supernatants were incubated with BT474 & SK-BR-3 cells. Multimer-loaded cells were then analysed by flow cytometry by measuring the mean fluorescence intensity of eGFP.

FIG. 6: Flow cytometry analysis of the relationship between FHR4 valence within trifunctional multimers and C3b activation levels on BT474 breast cancer cells. Trifunctional multi-FHR4/multi-$V_HH$ anti-Her2/mono-eGFP multimer-containing supernatants from 4 isolated single clones were analysed on BT474 target cells for their MFI for APC (C3b), PE (His) and eGFP. Multimer-loaded BT474 were then incubated in veronal buffer supplemented with NHS, and then simultaneously stained with a mouse anti-C3b mAb and a rabbit anti-His pAb, followed by an anti-mouse IgG APC-conjugated Ab and an anti-rabbit IgG PE-conjugated Ab. a) Analysis of the FHR4 densities on multimer-loaded BT474 targets. b) Analysis of the C3b deposition on multimer-loaded BT474 cells. c) The FHR4 valence of trifunctional heteromultimers from the 4 selected clones has been determined using their MFI/His signal. Bifunctional $V_HH$ anti-Her2/eGFP multimers with His tag represent the highest His valence which is 7, whereas the same bifunctional multimer with FLAG tag represents the lowest 0 valence for His. The MFI/His for the 4 clones are distributed between the 2 extreme values and the corresponding FHR4-valence is calculated from the curve.

FIG. 7: Biacore analysis of the FHR4-binding specificity for C3b and FB.

Curves representing the dose-response binding of C3b alone (triangles) or in the presence of Factor B (circles) on FH multi-FHR4/multi-$V_HH$ anti-Her2/mono-eGFP trifunctional heteromultimers. Multimer-bound C3b is depicted on the Y axis as number of response units (RU).

FIG. 8: Trifunctional multimer-mediated complement-dependent cytotoxicity.

Heteromultimer-mediated CDC was measured on Her2-positive SK-OV-3 ovarian carcinoma cells. SK-OV3 cells were incubated with different compounds: multi-FHR4/multi-2D3 $V_HH$ anti-Her2/mono-eGFP trifunctional heteromultimer (FH), Trastuzumab, Pertuzumab, FH and pertuzumab, and no drug. Cells were then incubated with veronal buffer supplemented with NHS. Cells were then stained extemporaneously with Propidium iodide (PI), prior to analysis using flow cytometry.

Figure 9:
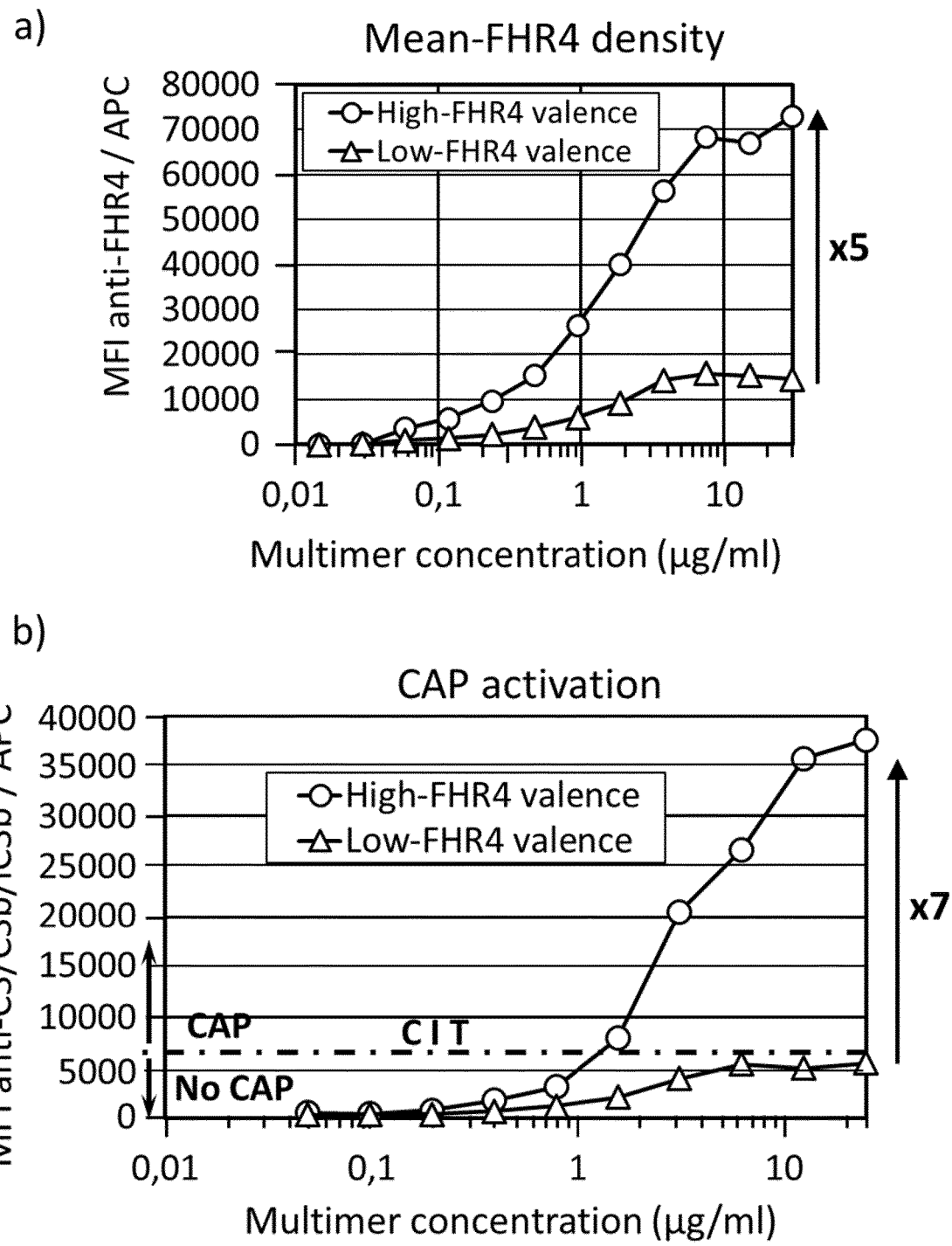

FIG. 9: Optimized heteromultimeric immunoconjugates overcome a Complement Inhibitory Threshold to elicit strong C3b deposit on SK-OV-3 cells.

Panel (a) represents a graph plotting the mean FHR4-valence on SK-OV-3 cells of optimized high-FHR4 and low-FHR4 valence multimers (multi-FHR4.C4bpα.His/multi -2D3 $V_HH$ anti-Her2.C4bpα.FLAG/mono-eGFP.C4bpβ) in function of the concentration of the purified multimer. Cells were then stained with a primary anti-FHR4, then a matching secondary Ab and then analyzed using flow-cytometry.

Panel (b) represents a graph plotting the ability of optimized high-FHR4 and low-FHR4 valence multimers (multi-FHR4.C4bpα.His/multi-2D3 $V_HH$ anti-Her2.C4bpα.FLAG/mono-eGFP.C4bpβ) to mediate C3b-deposits on target cells in function of the concentration of the purified multimer. Cells were then stained with a primary anti-C3b mAb, then a matching secondary Ab and then analyzed using flow-cytometry. The dashed line indicates the Complement Inhibitory Threshold (CIT) above which efficient CAP activation occurs.

Figure 10:
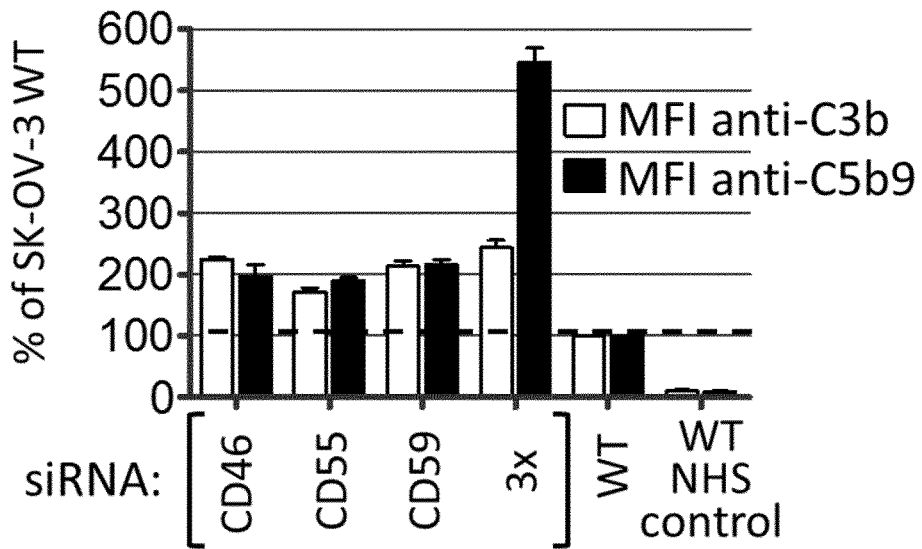
Figure 10:
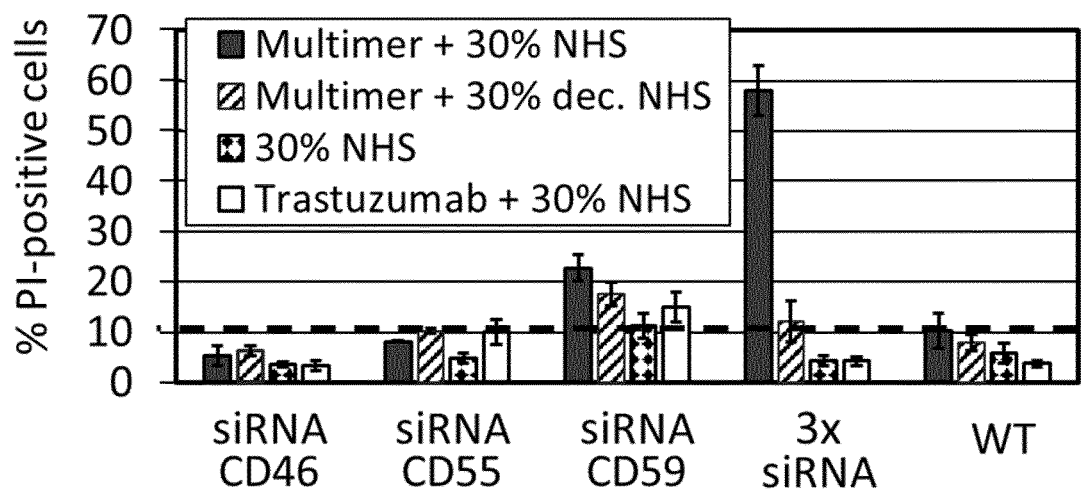

FIG. 10: FHR4-multimer-directed CAP activation, MAC formation and complement-dependent cytotoxicity on SK-OV3 tumor cells upon mCRPs knockdown.

a) Single (CD46, CD55 or CD59) mCRP-knockdown variants, triple (CD46, CD55 and CD59) mCRP-knockdown variants and SK-OV-3 wild type (WT) were incubated with optimized high-FHR4 valence multimers in the presence of normal human serum (NHS). Cells were then stained either with an anti-C3b/iC3b (7C12) or antiC5b9 (aE11) mouse mAbs, followed by a secondary Ab APC-conjugated. MFI for C3b or C5b9 corresponding to multimer-mediated C3b deposit and MAC formation were measured and expressed as percentage of the MFI for SK-OV-3 WT cells. Dashed line indicates multimer-mediated CAP activation and MAC formation levels for the reference SK-OV-3 WT; b) SK-OV-3 variants or WT were incubated with (i) multimers and 30% NHS, (ii) multimers and 30% decomplemented NHS, (iii) 30% NHS alone or (iv) Trastuzumab and 30% NHS. Multimer-mediated CDC was measured using flow cytometry as percentage of PI-positive cells. Dashed line indicates the percentage of PI-positive cells for SK-OV-3 WT when using the multimers and 30% NHS.

Figure 11:
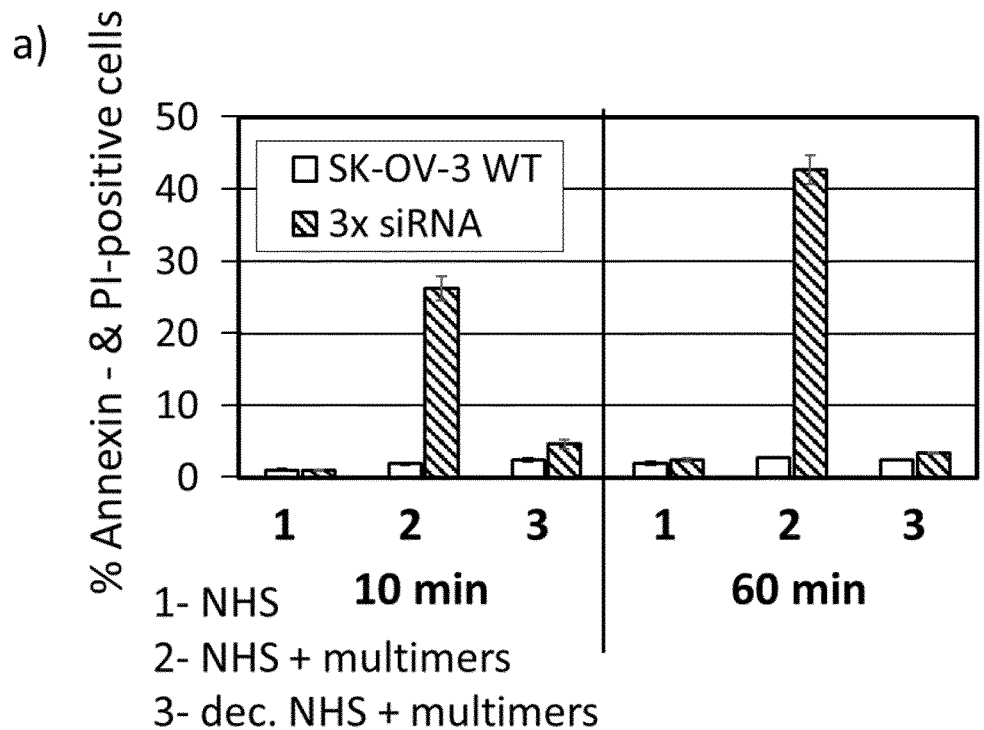
Figure 11:
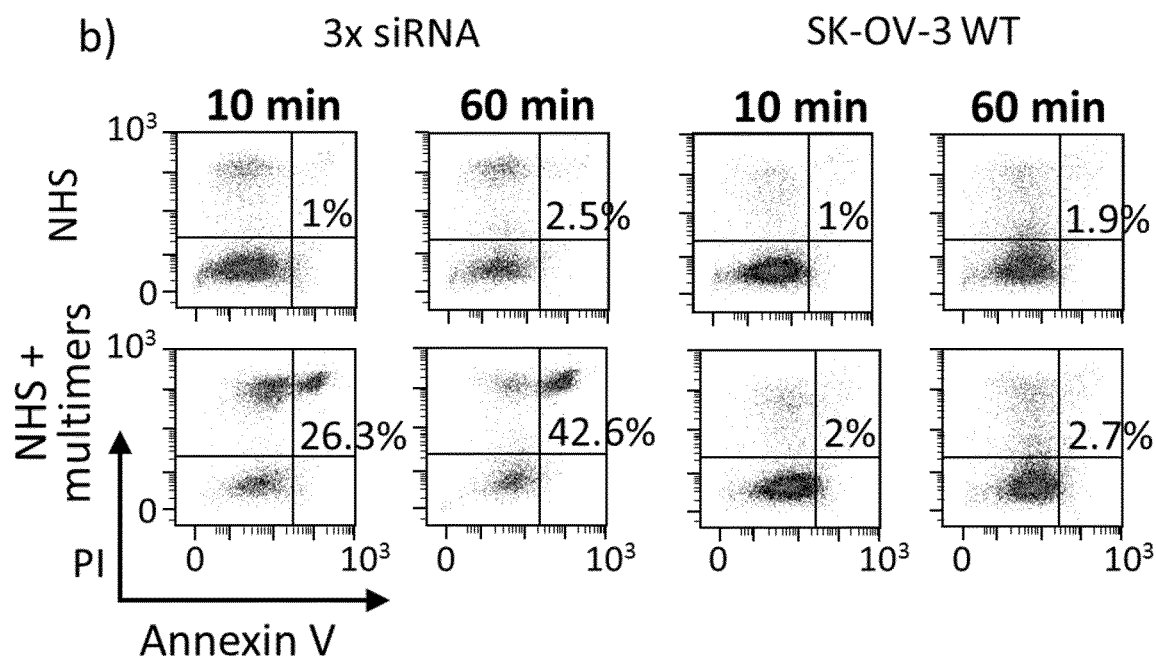

FIG. 11: Flow cytometry analysis of Annexin V-PI staining showed that multimer-directed CDC on SK-OV-3 mCRP-knockdown variants is a necrotic process. FHR4-directed complement-mediated cell death was analysed on SK-OV-3 WT cells incubated with 1) normal human serum (NHS), 2) NHS and 15 µg/ml the purified high-FHR4 valence trifunctional heteromultimers, or 3) decomplemented NHS and multimers. After 10 min or 60 min, the reaction was stopped in ice. Cells were then stained with PI/annexin V (AnV) and analysed by flow cytometry. Panel a) represents the percentages of cell staining positive for AnV and PI. Panel b) shows $PI^+/AnV^-$ (upper left quadrant) and $PI^+/AnV^+$ (upper right quadrant) staining representing primary necrotic cells and secondary necrotic/late apoptotic cells, respectively, which are depicted at 10 min and 60 min for 3×siRNA variant and SK-OV-3 WT, with NHS or NHS and multimers.

Figure 12:
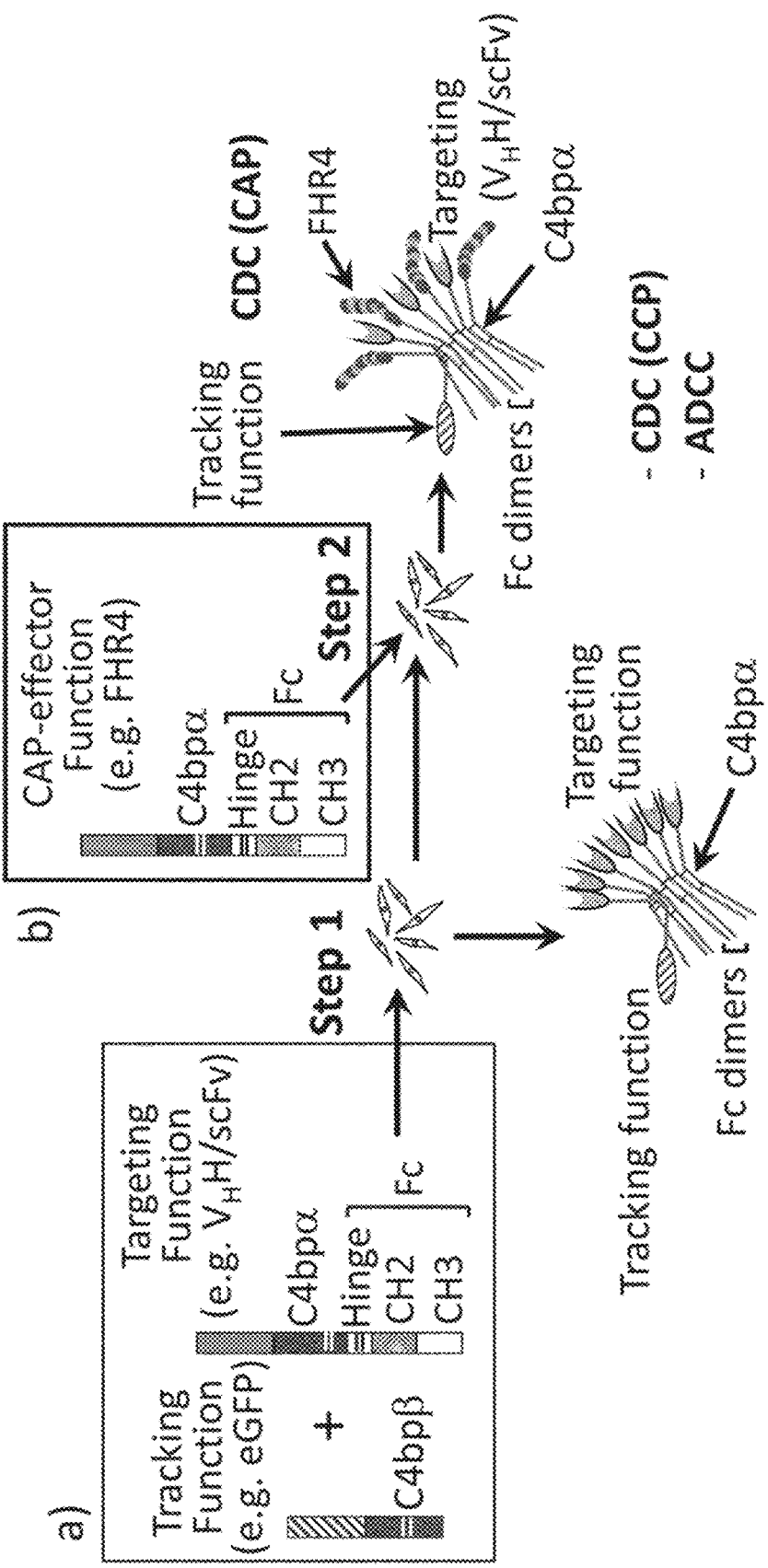

FIG. 12: Strategy to generate high FHR4-valence tetrafunctional heteromultimers with concomitant CDC and ADCC activities.

Step 1: Generation of the α-β trifunctional heteromultimers.

Co-transfection of cells with a) a nucleic acid vector encoding a targeting and an effector function (e.g. encoding $V_HH$ anti-Her2 upstream of C4bpα and the hinge, CH2 and CH3 domains of IgG ('Fc') downstream of C4bpα) and a nucleic acid vector encoding a tracking function (e.g. encoding eGFP upstream of C4bpβ) to generate 7α-1β trifunctional heteromultimers, for example, multi-$V_HH$ anti-Her2.C4bpα.Fc/mono-eGFP.C4bpβ trifunctional heteromultimer targeting Her2-expressing tumour cells. Step 1 also includes (i) an antibiotic selection, (ii) a subcloning and (iii) a screening to identify a clone expressing high amounts of trifunctional heteromultimers.

The addition of the Fc from IgG downstream from the C4bp C-terminal α-chain scaffold fragment allows Fc monomers within a single multimeric molecule to dimerise into Fc dimers.

Step 2: Generation of the α-α-β tetrafunctional heteromultimers. A selected cell clone expressing the trifunctional heteromultimers from Step 1 was co-transfected with a CAP-effector cassette (EFF) (e.g. comprising FHR4 upstream of C4bpα) and a plasmid for a second antibiotic selection to generate the tetrafunctional heteromultimers, for example, multi-FHR4.C4bpα.Fc/multi-$V_HH$ anti-Her2.C4bpα.Fc/mono-eGFP.C4bpβ tetrafunctional heteromultimers. Step 2 also includes (i) an antibiotic selection, (ii) a subcloning and (iii) a screening to identify a clone expressing tetrafunctional heteromultimers with low EF or high FHR4 valences.

These tetrafunctional heteromultimers displaying the Fc from IgG have the advantage to trigger ADCC and CDC at the same time, through Fc (ADCC) fragments and FHR4 (CDC) moieties.

Figure 13:
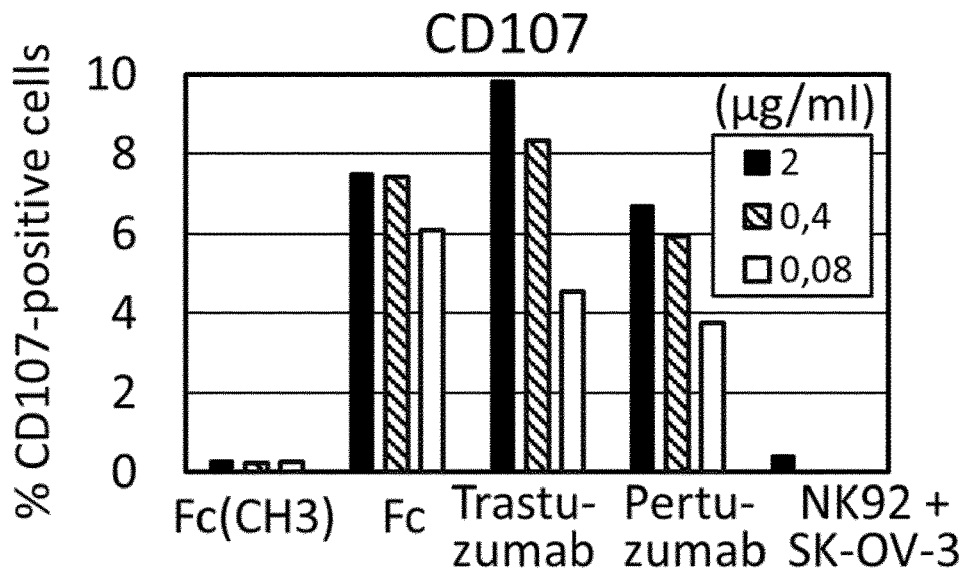
Figure 13:
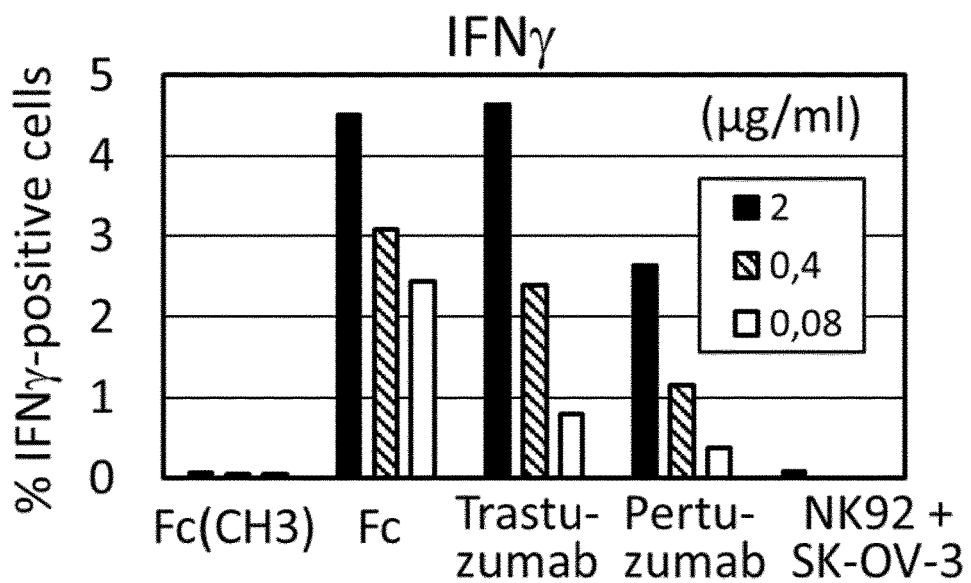

FIG. 13: Adding Fc from IgG as a functional moiety allowed multimer-mediated ADCC.

CD107 (a) and IFNγ (b) expression were analysed using flow cytometry for NK92-humCD16 effector cells incubated with SK-OV-3 cells (ratio E:T/5:1), which are incubated with 2, 0.4 and 0.08 µg/ml of control trifunctional heteromultimers ('Fc(CH3)') and $V_HH$ anti-Her2.C4bpα.Fc/eGFP.C4bpβ trifunctional heteromultimer CFO. As negative control, SK-OV-3 cells that were not previously incubated with the multimers are incubated with NK92-humCD16 cells. Trastuzumab and pertuzumab were used as positive controls instead of the multimers at same serial dilutions.

DETAILED DESCRIPTION OF THE INVENTION

Before the present method and devices used in the invention are described, it is to be understood that this invention is not limited to particular methods, molecules, or uses described, as such methods, molecules, or uses may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes"

or "containing", "contains", and are inclusive or open-ended and do not exclude additional, non-recited members, elements or method steps.

The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present invention provides methods for preparing multifunctional heteromultimeric protein complexes, the multifunctional heteromultimeric protein complexes themselves and uses thereof. More particularly, the present invention concerns methods for preparing multifunctional heteromultimers with a defined ratio of functional components by means of several successive selection steps and multifunctional heteromultimeric protein complexes displaying two or more functional components of which at least one is a tracking component. A fixed number of tracking components is used to determine the number of each functional component present in the multimers.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "multifunctional" as used herein, refers to the possession of or ability to perform two or more different functions or to be used in different ways. The multifunctional molecule according to present invention can be bifunctional, trifunctional, tetrafunctional, or carry up to eight distinct functions. The different functionalities are contained within the different components present in the multifunctional heteromultimeric protein complex, more specifically, one or more targeting components which give the ability to bind to a target cell, one or more effector components which can mediate a desired effect and one or more tracking components which allow detection of the complex.

The term "multimer" as used herein, refers to an aggregate of multiple molecules (e.g. monomers) that are held together with non-covalent bonds. This distinguishes multimers from polymers, which are multiple monomers held together with covalent bonds. The terms "multimerizing" and "multimerization" according to present invention refer to the process of assembling multimers of given molecule. For proteins, the assembly of protein subunits results in multimeric protein complex with a quaternary protein structure. The term "heteromultimer" or "heteromultimeric" as used herein refers to a composition comprising more than one molecule, wherein at least two molecules differ from each other. For polypeptides, this difference is in amino acid sequence by at least one amino acid residue.

The term "complex" as used herein, refers to a group of two or more identical or different components held together by chemical forces.

Accordingly, in a first aspect of the invention methods are provided for preparing multifunctional heteromultimeric protein complexes with a defined ratio of functional components, which comprise successive transfection of host cells with different nucleic acids encoding multimerizing scaffold proteins fused to functional components (the term "functional component" is defined herein below). Indeed, the methods provided herein involve the use of multimerizing scaffold proteins which will associate into a multimeric protein upon expression in a host cell. The multimerizing scaffold proteins of the multimeric protein may all be different, or at least two multimerizing scaffold proteins of the multimeric protein may be identical, for example, the C4bp multimerizing scaffold comprises 7 identical α-chains and one unique β-chain. More particularly, the methods comprise the following successive steps:

(a) co-transfecting host cells with a nucleic acid vector that encodes a first functional component which is a tracking component fused to a first multimerizing scaffold polypeptide, and with a nucleic acid vector that encodes a second functional component, different from said tracking component, fused to a second multimerizing scaffold polypeptide; (b) expressing the multimerizing scaffold peptides and allowing them to multimerize into bifunctional multimers, comprising a fixed number of one or more tracking component and said second functional component; (c) selecting the single-cell clones that secrete the bifunctional multimers; (d) transfecting said clones with a nucleic acid vector that encodes a third functional component different from said second functional component and said tracking component fused to a third multimerizing scaffold polypeptide and, optionally, simultaneously or subsequently with a nucleic acid vector that encodes a fourth functional component different from said tracking component and from said second and third functional component fused to a fourth multimerizing scaffold polypeptide, optionally further with a nucleic acid vector that encodes a fifth functional component different from said tracking component and from said second, third and fourth functional component fused to a fifth multimerizing scaffold polypeptide, with a nucleic acid vector that encodes a sixth functional component different from said tracking component and from said second, third, fourth and fifth functional component fused to a sixth multimerizing scaffold polypeptide, with a nucleic acid vector that encodes a seventh functional component different from said tracking component and from said second, third, fourth, fifth and sixth functional component fused to a seventh multimerizing scaffold polypeptide and/or with a nucleic acid vector that encodes an eighth functional component different from said tracking component and from said second, third, fourth, fifth, sixth and seventh functional component fused to an eighth multimerizing scaffold polypeptide; (e) expressing the multimerizing scaffold polypeptides and allowing them to multimerize into multimers comprising a fixed number of one or more tracking components and one or more of said second and third and optionally one or more of said fourth, fifth, sixth, seventh and/or eighth functional component; (f) selecting single-cell clones secreting multimers having the desired relative ratio of second, third and optionally fourth, fifth, sixth, seventh and/or eighth functional components; and (g) recovering from said clones the produced multimeric protein complexes.

In particular embodiments of the method for preparing multifunctional heteromultimeric protein complexes with a defined ratio of functional components as described herein, in step (a); a second and third functional component are fused to the second multimerizing scaffold polypeptide. It will be clear to the skilled person that if step (a) relates to a nucleic acid vector that encodes a first functional component which is a tracking component fused to a first multimerizing scaffold polypeptide and to a nucleic acid vector that encodes a second and third functional component, different from said tracking component, fused to a second multimerizing scaffold polypeptide that in the method described above, trifunctional multimers are expressed and selected in step (b) and (c), respectively. Consequently, any additional functional components in steps (d) and so forth are named the "fourth" and so forth functional component whereas any multimerizing scaffold proteins remain named "the third" and so forth. In further particular embodiments of the method described above, the nucleic acid vector of step (d) encodes more than one functional component fused to one multimerizing scaffold polypeptide, preferably two functional components. In preferred embodiments, all nucleic acid vectors in step (d) encode two functional components. In even more preferred embodiments, at least one of the functional components encoded by the nucleic acid vector in step (d) is the same in all said nucleic acids. In the most preferred embodiment, at least one of the functional components encoded by the nucleic acid vector in step (d) is the same in all said nucleic acid vectors, and is the same as the second or third functional component in step (a). It will be clear to the skilled in the art that the naming of the "$X^{th}$" function would follow logic numbering as the case will be.

The methods thus encompass transfecting host cells with one or more vectors comprising a polynucleotide sequence encoding a multimerizing scaffold polypeptide fused to a functional component. In particular embodiments, the sequence encoding a multimerizing scaffold polypeptide is fused directly to the sequence encoding the functional component. In particular embodiments, however, the sequence encoding a multimerizing scaffold polypeptide and the sequence encoding the functional component are separated by a linker sequence. Linkers are short peptide sequences that are often composed of flexible residues like glycine and serine so that the adjacent protein domains are free to move relative to one another. Longer linkers are used when it is necessary to ensure that two adjacent domains do not sterically interfere with one another, e.g. when the functional domain is large. The length of the linker is typically between 5-30 amino acids. An example is the pentapeptide GGGGS (or G4S or Gly4Ser) and multimers thereof, such as the 15-mer (G4S)3.

In particular embodiments, step (a) is performed as with a single transfection using a bi-cistronic vector encoding both the first and second functional component, each fused to a multimerizing scaffold polypeptide. Furthermore, step (d) can be performed by simultaneous or subsequent transfections, optionally, one or more of these transfections are performed using a multi-cistronic vector encoding two or more functional components, each fused to a multimerizing scaffold polypeptide. The skilled person will understand that when using multi-cistronic vectors, the number of transfections and nucleic acid vectors required to obtain clones secreting multimers having the desired relative ratio of second, third and fourth, and optionally, fifth, sixth, seventh or eighth, functional components decreases.

The skilled person will understand that in the methods envisaged herein, the optional transfection with additional nucleic acid vectors such as described under (d) above, which is performed simultaneously or subsequently, can be carried out using (X-3) additional nucleic acid vectors that each encode an $X^{th}$ functional component different from said tracking component and said other functional component fused to an $X^{th}$ multimerizing scaffold polypeptides, wherein X is preferably a number between 4 and 20 and is at most the number of polypeptides present in the multimerizing scaffold. For example, when the multimerizing scaffold is a pentamer, X is 5, when the multimerizing scaffold is an octamer, X is 8. In particular embodiments where more than one functional component is fused to a multimerizing scaffold polypeptide, the number of functional components present in the multimerizing component can be higher than the number of polypeptides present in the multimerizing scaffold.

In particular embodiments, the methods for preparing multifunctional heteromultimeric protein complexes lead to the formation of a multimeric protein complex comprising 1, 2, 3, 4, 5, 6, 7, 8, 9, 10, 11, 12, 13, 14, 15, 16, 17, 18, 19, 20 different functional components, preferably 3 or 4, more preferably 4. In particular embodiments where more than one functional component is fused to a multimerizing scaffold polypeptide, the preferred number of different functional components present in the multimeric protein complex is 4 or 5, more preferably 4.

The methods provided herein are characterized in that they allow the provision of multifunctional heteromultimeric protein complexes with a defined ratio of functional components. The term "ratio" or "relative ratio" as used herein refers to the proportion between two or more different components of the multimeric protein complexes. In the present invention, for instance, the ratio can be used to indicate the quantitative relationship between the tracking component and the other functional components in a given multimer. It is represented by at least two numbers separated by a colon (":"), the number preceding (the first) colon representing the tracking component and the numbers following (the first and optionally additional) colon(s) each representing a different functional component. However, given that the tracking component is present in a fixed number (and is typically 1), this may be left out, such that the ratio only represents the relative number of the remaining functional components. By tagging the different components either directly (e.g. incorporating a tag in the component structure) or indirectly (e.g. after expression), and measuring the signal generated by the tags of each of the functional components relative to the tracking component, the ratio of the different components in a multimer can be determined. For instance, as will be detailed below, in particular embodiments, the tracking component comprises a fluorescent tag and each of the other functional components is tagged by a (different) fluorescent-tagged monoclonal antibody (either directly or indirectly binding to the functional component). By use of FACS analysis, the ratio of mean fluorescence intensity (MFI) of a specific fluorescent tagged antibody capable of specifically detecting a functional component and the MFI of the fluorescent tag of the tracking component can be calculated. Because of the fixed number of tracking components, this method allows to estimate the relative number of each different functional component present in the complex.

In particular embodiments, each of the different tracking and functional components is tagged by a different tag, and the ratio of the different components in the multimer is determined through FACS analysis.

In particular embodiments, the ratio of the different components in the multimer is determined by SDS-PAGE and staining of the recovered multimers by a stain suitable for detection and quantification of proteins separated by PAGE (e.g. SYPRO®-Ruby staining), and measuring the intensity of the different molecular species using the technic of calculation of the area under the curve. It this manner it would be possible to determine the percentage of the total of each molecular species. Preferably, the staining suitable for the detection of proteins separated by PAGE is a fluorescent stain, more preferably SYPRO®-Ruby staining. Preferably, the staining is performed under non-reducing conditions. In particular embodiments, the multimers were purified before staining thereof.

The specific ratio of the different functional components in the multimers envisaged herein will depend on the application envisaged. The importance is that multimers can be provided with a well-defined ratio of different functional components. Accordingly, for instance, in particular embodiments the methods of present invention can be used to obtain multimers comprising, in addition to one tracking component, two other functional components (a second and a third functional component), wherein the relative ratio of the tracking component, the second functional component and the third functional component can be represented as 1:N:M, wherein N represents the second functional component and M represents the third functional component and wherein the sum of N and M is at least 2, at least 3, at least 4 or at least 5, such as 10 and wherein the ratio is, for example, selected from 1:9:1, 1:8:2, 1:7:3, 1:6:4, 1:5:5, 1:4:6, 1:3:7, 1:2:8, 1:1:9, 1:8:1, 1:7:2, 1:6:3, 1:5:4, 1:4:5, 1:3:6, 1:2:7, 1:7:1, 1:6:2, 1:5:3, 1:4:4, 1:3:5, 1:2:6, 1:1:7, 1:6:1, 1:5:2, 1:4:3, 1:3:4, 1:2:5, 1:1:6, 1:5:1, 1:4:2, 1:3:3, 1:2:4, 1:1:5, 1:4:1, 1:3:2, 1:2:3, 1:1:4, 1:3:1, 1:2:2, 1:1:3, 1:2:1, 1:1:2, or 1:1:1. Similar ratios can be envisaged for tetrafunctional multimers and multimers with a higher number of functional components. It will be understood that the methods of the invention are of particular interest for obtaining multimers with very high or low ratios of certain functional components. For instance, in view of the representation of the relative ratio of the tracking component, the second functional component and the third functional component in multimers comprising 3 different functional components as described above (i.e. 1:N:M, wherein N represents the second functional component and M represents the third functional component), a ratio of 1:6:1 represents a high ratio for the second functional component and a low ratio for the third functional component, while a ratio of 1:1:6 represents a high ratio for the third functional component and a low ratio for the second functional component.

The methods of the present invention are based on the ability to determine the number of functional components relative to a fixed number of tracking components. The term "fixed" as used herein refers to the fact that for a certain batch of multimers being prepared in each of the multimers the number of tracking components will be the same. This is necessary in order to allow for the relative determination of the other functional components. The methods according to the invention thus require that the assembly of the multimer always include a fixed number of the multimerizing scaffold peptides comprising the tracking component. In particular embodiments, this is ensured by the use of multimerizing polypeptide scaffolds which are known to associate in a given way. "Scaffold protein" and "scaffold polypeptide" as used herein are used interchangeably and refer to structural components of which the scaffold is built. Scaffold proteins or peptides typically can have a secondary structure such as an alpha-helix, beta-sheet or coils. For instance, a typical example of a multimerizing scaffold protein are the alpha and beta-chains of the C4bp multimer, which associate in a well-defined way. While the C4bp multimer can comprise different alpha-chains, when alpha and beta chains are expressed together, the multimer will always only comprise one beta-chain. Alternatively it can be envisaged that the tracking component is incorporated into the backbone of a multimer scaffold. The methods of the invention are typically most suitable for multimerizing scaffold proteins which can freely multimerize into multimers comprising at least 3, preferably between 4 and 20 scaffold proteins, but higher numbers of multimerizing proteins can also be envisaged.

In particular embodiments, the multimerizing scaffold proteins of the multimeric protein are all different. In particular embodiments, at least 2, at least 3, at least 4, at least 5, at least 6, at least 7, preferably 6 or 7, multimerizing scaffold proteins of the multimeric protein are identical.

In particular embodiments, the second multimerizing scaffold polypeptide as described in step (a) is different from the first multimerizing scaffold polypeptide as described in step (a). In particular embodiments, the second multimerizing scaffold polypeptide as described in step (a) is identical to the third and optionally fourth multimerizing scaffold polypeptide as described in step (d).

A preferred embodiment of the invention involves the use of a C4bp heteromultimer. The C4bp molecule has an octopus-like structure made of seven branching α-chains and one central β-chain. Each chain contains short consensus repeat (SCR). Each SCR of about 60 amino acids includes two intra-chain disulfide bridges. The C-terminal part of the C4bp lacks biological function and is responsible for the polymerization of the molecule in the cytoplasm of C4bp producing cells. The β-chain subunit is not required for the oligomerization of the α-chains. The C-terminal part of the α-chain of C4bp is preferred to set up homo and hetero multimers, due to these properties as well as to its non-immunogenicity of a normal human plasma protein. The method for multimerizing glycoproteins based on the use of about 60 amino acid C-terminal domains of the C4bp alpha-chain (C4bpα) or beta-chains (C4bpβ) as covalent scaffolds for multimerisation, was previously described by Libyh et al. (3). In particular embodiments, the methods provided herein involve the use of C4bpα comprising the 174 bp gene encoding the 58 amino acids of the C4bpα (ref. UniProt n° P04003) and C4bpβ comprising the 171 bp gene encoding the 57 amino acids of the $3^{rd}$ short consensus repeat of the C4bp β-chain, followed by the 177 bp encoding the 59 amino acids of the C4bpβ (ref. UniProt n° P20851). It will be clear to the skilled person that the methods provided herein can involve the use of C4bp heteromultimer of any animal species forming a C4bp heteromultimer with the same properties as the human C4bp heteromultimer. In particular embodiments, the C4bp proteins forming the C4bp heteromultimer are homologous of the human C4bp proteins. Preferably, the C4bp heteromultimer consists of mammalian C4bp proteins, for example, rodent (e.g. mouse, rat, guinea pig) C4bp proteins, rabbit C4bp proteins, bovine C4bp proteins, pig C4bp proteins or human C4bp proteins, more preferably, human C4bp proteins.

Other examples of scaffold proteins that can be used are ficolin, collectin, Mannose Binding Protein, C1q, or IgM scaffolds.

As described above, to allow for the relative determination of the other functional components, the number of tracking components in each of the multimers of a certain batch of multimers needs to be the same. In particular embodiments, the multimerizing scaffold is one that preferably multimerises into multimers when at least two different types of multimerizing scaffold polypeptides are present. More preferably, at least one of said different types of multimerizing scaffold polypeptides is present in the multimer as a single multimerizing scaffold polypeptide. The tracking component can be cloned into said single multimerizing scaffold polypeptide and this allows for the relative determination of the other functional components. For instance, the C4bp protein invariably comprises only one beta-chain, hence binding the tracking component to C4bpβ would permit to determine the ratio of functional components. In particular embodiments of the method of present invention, the tracking component is fused to the beta-chain of C4bp, preferably the c-terminal part of a beta-chain of C4bp. Another example is the IgM scaffold, because the J chain in the IgM is unique and leads to a pentameric association of the other arms forming the IgM, the tracking function could be cloned into the J chain. In particular embodiments of the method of present invention, each targeting component is fused to the alpha-chain of C4bp. In particular embodiments of the method of present invention, each effector component is fused to the alpha-chain of C4bp.

In particular embodiments, each alpha-chain of C4bp is fused to two functional components. In more particular embodiments, a first functional component is located upstream and a second functional component is located downstream of the alpha-chain of C4pb. In even more particular embodiments, one of the functional components fused to the alpha-chain of C4pb is monomeric Fc.

In a preferred embodiment, if a C4bp heteromultimer is used as multimerizing scaffold in the methods of present invention and if the presence of only one tracking component is envisioned, the relative ratio of the tracking component, the second functional component (N) and the third functional component (M) in multimers comprising 3 different functional components as described above can be represented as 1:N:M, wherein the sum of N and M is 7.

The methods of the invention are aimed at producing multifunctional multimers, e.g. comprising different functional components. The term "functional component" as used herein, refers to an element which can exert a given function. In present context, three main functions are distinguished: tracking function (further detailed below), effector function and targeting function, but the invention is not limited thereto. The term "targeting function" as used herein refers to the ability of a component to ensure the binding of the multimer to a given target such as a given cell type or molecule. The term "effector function" as carried out by an "effector component" as used herein refers to the ability to affect another molecule and/or regulate the biological activity of a target cell. For example, effector molecules can have enzyme activity or affect the activity, gene expression, or cell signaling of a target cell.

Examples of targeting and effector components are known to the skilled person and will be detailed below. Typical examples of targeting components are antibodies, such as antibodies (or fragments or derivatives thereof) directed against cell surface antigens, or soluble receptors (e.g. soluble CR1) or ligands interacting with cell-surface molecules. The targeting components can also be a ligand involved in the immune check points (e.g. PD-1, PD-L1 and CTL-A4). Typical examples of effector components are cytokines (e.g. IL2, IL15), growth factors, hormones, vaccine antigens, toxins (e.g. Tetanus toxin fragment C, anatoxic fragment of diphtheria toxin), enzymes, or a self-antigen against which natural antibodies exist. Further examples of effector moieties include antigenic cytoskeleton proteins (e.g. actin, tubulin), or antigenic components and other proteins such as regulators of the complement system. Still further examples of effector moieties include antibodies, such as antibodies or fragments or derivatives thereof (e.g. monomeric Fc, preferably monomeric Fc of IgG comprising the hinge and CH2 and CH3 domains of IgG).

Generally, the functional components can be synthetic or natural peptides, biological macromolecules, polypeptides, proteins, peptide analogues, peptide mimetics, antibodies, antibody fragments and derivatives thereof.

The term "antibody" as used herein includes full length antibodies (e.g. monoclonal antibodies, polyclonal antibodies), chimeric antibodies, multivalent antibodies, multi-specific antibodies (e.g., bispecific antibodies) antibody fragments (e.g., Fab, F(ab')$_2$ and Fv, or monomeric Fc, preferably monomeric Fc of IgG comprising the hinge and CH2 and CH3 domains of IgG), single chain molecules and diabodies. Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (5,6). Five human immunoglobulin classes are defined on the basis of their heavy chain composition, and are named IgG, IgM, IgA, IgE, and IgD. The IgG-class and IgA-class antibodies are further divided into subclasses, namely, IgG1, IgG2, IgG3, and IgG4, and IgA1 and IgA2. The heavy chains in IgG, IgA, and IgD antibodies have three constant region domains, that are designated CH1, CH2, and CH3, and the heavy chains in IgM and IgE antibodies have four constant region domains, CH1, CH2, CH3, and CH4. Thus, heavy chains have one variable region and three or four constant regions.

The term "antibody fragments" as used herein refers to only a part of an intact antibody, wherein that preferably preserves at least one, preferably most or all, of the functions normally associated with that part when present in an intact antibody. Antibody fragments include Fv, Fv', Fab, Fab', and F(ab') fragments. Typically at least the antigen-binding function of the antibody is maintained and the fragment is referred to as an antigen-binding antibody fragment.

In particular embodiments, one or more of the functional components is a targeting component. In particular embodiments, the one or more targeting components are selected from the group consisting of antibodies, antigen-binding fragments thereof, ligands of a target cell receptor, and soluble receptors. For instance, antibodies or antibody fragments can have significant binding affinity for surface molecules of a target cell of interest. These surface molecules can be, for example, T cell surface molecules, B cell surface molecules, tumor-associated antigens (e.g. Human Epidermal growth factor Receptor 2 (HER2)/neu, CTLA-4, EGFR, CD5, CD, G250), and molecules expressed on the surface of infected target cells (e.g., viral proteins such as GP120), preferably HER2/neu.

The targeting component envisaged in the context of the present invention can also be immunoglobulin (Ig) molecules of irrelevant specificity (or immunoglobulin molecule fragments that include or contain only an Fc portion) that can bind to an Fc receptor (FcR) on the surface of a target cell, preferably a tumor cell.

The targeting component can further be ligands for signal transduction receptors (e.g., CD40 ligand, an MHC class I molecule or fragments of an MHC molecule involved in binding to CD8, an MHC class II molecule or the fragment of an MHC class II molecule involved in binding to CD4), or ligands for adhesion receptors, e.g., ICAM-1, ICAM-2, or fibronectin or a domain (e.g., one containing one or more of the "Arg-Gly-Asp" repeats) of fibronectin involved in binding to integrin molecules. In addition a targeting domain could be Fas or Fas ligand or other death domain containing polypeptides (e.g., members of the TNF receptor family) or ligands for such polypeptides (e.g., TNF-alpha, or TWEAK).

In particular embodiments, at least one of the targeting components is multi-2D3 $V_HH$ anti-HER2 or scFv anti-GYPA.

It will be clear to the skilled person that target-binding molecules, such as, but not limited to, the antibodies described above, can act as effector and/or targeting molecules. The functional components can thus comprise target-binding molecules, whereby the nature of the target (and optionally the effect of the binding of the functional component therewith) will determine whether the functional component is considered a "targeting component" and/or an effector component. For example, a multifunctional heteromultimeric protein complex comprising monomeric Fc as one of its functional components, and when present in at least two polypeptides of the heteromultimeric protein complex, could bind a natural killer (NK) cell by dimerization of the monomeric Fc and the effect of the binding of the Fc dimer to the NK cell could lead to activation of the NK cell.

In particular embodiments, at least one, preferably at least two, of the functional components is a monomeric Fc.

The methods of the present invention make use of tracking components which are incorporated into the multimeric protein in a defined number. The tracking components are characterized in that they can be specifically detected in a quantitative way. In particular embodiments, this implies that the tracking component comprises a tag which can be directly detected. Examples of suitable tags include but are not limited to fluorescent dyes (e.g. fluorescein, fluorescein-isothiocyanate (FITC), Texas red, rhodamine, green fluorescent protein, enhanced green fluorescent protein and related proteins with other fluorescence emission wavelengths, lissamine, phycoerythrin, Cy2, Cy3, Cy3.5, Cy5, Cy5.5, Cy7, FluorX [Amersham], SYBR Green I & II [Molecular Probes], and the like). Alternatively the tag can be a molecule which can be indirectly detected such as, biotin for staining with labelled avidin or streptavidin conjugate, an enzymes (e.g. luciferases, hydrolases, particularly phosphatases such as alkaline phosphatase, esterases and glycosidases, or oxidoreductases), substrates, cofactors, chemiluminescent groups, chromogenic agents, and colorimetric labels such as colloidal gold or coloured glass or plastic (e.g. polystyrene, polypropylene, latex, etc.), protein particles or beads. In particular, all detectable labels well known to those skilled in the art may be used as detectable labels for use in the present invention.

In the methods provided herein, in addition to the tracking component, the relative expression of the other functional components, such as targeting and effector components, which is indicative of their ratio when assembled into a multimer, is also detected. It can be envisaged that tags are linked directly to the functional components or to the multimerizing scaffold protein, such as by linking to a polypeptide of the multimer. In order to differentiate between the tracking component and the other functional components within a multimer, the tags used for the detection of each of the different components is preferably different. For practical purposes it is of interest that different tags can be detected with a similar detection method. For instance, in particular embodiments, the different tags are all fluorescent labels.

The inventors have developed particular methods which allow to ensure the provision of multifunctional heteromultimeric protein complexes as described herein. Typically these methods involve the following steps. Host cells are transfected with nucleic acids encoding different functional components, of which one is a tracking component, each fused to a multimerizing scaffold polypeptide. Next, the encoded tracking component and other functional components, each fused to a multimerizing scaffold polypeptide, are expressed by the host cell and are allowed to multimerize into heteromultimeric protein complexes. Subsequently, the complexes are secreted by or isolated from the host cell and optionally purified and concentrated.

Methods of transfection of foreign DNA into a host cell are known in the art and can involve instruments (e.g. electroporation, biolistic technology, microinjection, laserfection, opto-injection) or reagents (e.g. lipids, calcium phosphate, cationic polymers, DEAE-dextran, activated dendrimers, lipofectamine or magnetic beads), can be virus-mediated or by any other means known by the skilled person. In stable transfections, cells have integrated the foreign DNA in their genome. In transient transfections, the foreign DNA does not integrate in the genome but genes are expressed for a limited time (24-96 h). The term "co-transfecting" refers to the delivery of at least two different polynucleotides to the cell at the same time; in particular embodiments, this implies contacting the cell with two nucleic acid vectors comprising different DNA segments, at the same time. Alternatively, as described in Step 1 of FIG. 1, TaF and TrF cassettes can be cloned in a single bi-cistronic vector for stable expression of recombinant functional components in mammalian cells. This vector can have two separate identical or different promoters, each one driving the translation of a single gene, as depicted in FIG. 2 c. This expression vector can alternatively feature a unique promoter downstream which the first TaF or TrF cassettes is cloned, followed by an internal ribosome entry sites (IRES), or any other nucleotide sequence fulfilling the same function, downstream which the second TaF or TrF cassette is cloned. Moreover, this vector can contain an antibiotic resistance gene. In both cases, a single transfection is performed. If this vector does not display an antibiotic resistance gene, the latter can be provided in a separate expression vector that is cotransfected with the unique bicistronic vector containing TaF and TrF. These alternatives are also true for Step 2B, where 2 EF cassettes, featuring identical or preferentially distinct effector functions, are cotransfected. These 2 effector genes can be cloned in the same expression vector as described above, and as depicted in FIG. 2 d.

The term "nucleic acid vector" or "vector" as used herein, is a tool that allows or facilitates the transfer of an entity from one environment to another. It is a replicon, such as a plasmid, phage, or cosmid, into which another DNA segment may be inserted so as to bring about the replication of the inserted segment. In present application, a vector is a nucleic acid molecule capable of transporting another nucleic acid to which it has been linked. One type of vector is a "plasmid" which refers to a circular double stranded DNA loop into which additional DNA segments can be ligated. Another type of vector is a phage vector. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" can be used interchangeably as the plasmid is the most commonly used form of vector. The term 'multi-cystronic vector' or 'polycystronic vector' as used herein, refers to a vector that simultaneously expresses two or more separate proteins. This vector can have two or more separate identical or different promoters, each one driving the translation of a single gene. Alternatively, this expression vector can feature a unique promoter driving the translation of several genes. In both cases, a single transfection is performed. Preferably, the multi-cystronic vector is a bi-cystronic vector, expressing two separate proteins.

The term "host cell" as used herein, refers to the cell that has been introduced with one or more polynucleotides, preferably DNA, by transfection. Most commonly used host cells for production of proteins are mammalian immortalized cell lines such as CHO and HEK 293 cells, preferably HEK 293 cells, which allow easy transfection and have a high proliferation rate which facilitates the protein production and increases the yield. Large-scale production of protein complexes typically requires host cells capable of growing in suspension, such as suspension-adapted CHO and HEK 293 cells, preferably suspension-adapted HEK 293 cells. Alternatively, bacteria could serve as host cells.

The assembly of the multimerizing scaffold polypeptides by the host cell into a multimer typically depends on the nature of the multimerizing scaffold polypeptides used and the relative number of different polypeptides expressed. Typically, multimers are formed by random association of multimerizing scaffold polypeptides, irrespective of whether or not these comprise additional features such as functional or tracking components. In the context of the present invention, it may be desirable that the multimer either comprises a fixed backbone or naturally incorporates a fixed number of one type of multimerizing scaffold protein, which can be used to incorporate the tracking component into the multimer. However, typically the association of the remainder of the multimerizing scaffolds and their number will be random.

To obtain multifunctional heteromultimeric protein complexes with a defined ratio of functional components, it is necessary to select the host cells which generate a multimer comprising the functional components in the desired ratio.

The methods of the present invention typically involve two types of selection steps. In a first step, the method may comprise selecting the cells that have been successfully transfected with one or more nucleic acids encoding the multimerizing scaffold proteins. In particular embodiments, each of the multimerizing scaffold proteins which is linked to a different functional component comprises a different marker gene, such that it can be determined whether or not the cell is capable of expressing the different nucleic acids based on the expression of the marker genes. Typically marker genes are used that confer resistance to a compound, which is added to the culture medium, and will eliminate untransfected cells but not the transfected cells (positive selection, e.g. resistance to antibiotics). For example, selection antibiotics can be geneticin, zeocin, hygromycin B, puromycin or blasticidin. Antibiotics and their coding sequences are typically incorporated into the nucleic acid vector used for delivering genetic material into a target cell. A selection of the host cells can be based on the detection of the gene or gene product of interest in the host cell. This can be achieved by standard DNA, RNA and protein detection methods such as (quantitative) RT-PCR analysis, Serial Analysis of Gene Expression (SAGE), DNA microarray, RNA Seq, Tiling arrays, Northern blot, Western blot, protein immunoprecipitation, FACS analysis, fluorescent in situ hybridization (FISH), enzyme assays, microscopy and any other method known by the skilled person.

Additionally or alternatively, the detection of expression products can also be determined using tags or labels which can be detected directly or indirectly.

In a particular embodiment, the tag is a peptide sequence which is grafted onto the scaffold polypeptide or functional protein. While tags can be attached to proteins for various purposes, such as purification (e.g poly (His) tag), to assist proper protein folding (e.g. thioredoxin), separation techniques (e.g. FLAG-tag), or enzymatic or chemical modifications (e.g. biotin ligase tags, FlAsH), in the context of the present invention their main purpose is detection. Indeed, these tags can typically be visualized either directly or indirectly through detection with a labeled antibody or other protein or molecule binding or interacting with the tag. Examples of such tags are AviTag, Calmodulin-tag, polyglutamate tag, E-tag, FLAG-tag, HA-tag, His-tag, Myc-tag, S-tag, SBP-tag, Softag 1, Softag 3, Strep tag, TC tag, V5 tag, VSV-tag, Xpress tag, Isopeptag, SpyTag, Biotin Carboxyl Carrier Protein, Glutathione-S-transferase-tag, Green fluorescent protein tag, Halo-tag, Maltose binding protein-tag, Nus-tag, Thioredoxin-tag or Fc-tag, but is not limited thereto. Preferably, FLAG-tag, His-tag or Myc-tag.

Accordingly, in particular embodiments, the selection step of the methods provided herein comprises selecting the cells based on the detection of specific tags which are indicative of expression of the corresponding tagged scaffold polypeptides. Indeed, in particular embodiments second, third and optionally fourth up to $X^{th}$ functional components or each of said second, third and optionally fourth up to $X^{th}$ multimerizing scaffold polypeptides are expressed as tagged polypeptides and detection of the tags allows determining the number of each of said components or of each of said polypeptides relative to said tracking component or said first multimerizing polypeptide in said multimer, wherein X is a natural number between 4 and 20 and is at most the total number of polypeptides present in the multimerizing scaffold. More particularly it is envisaged that the tracking component and the other functional components each comprise a different tag. In more particular embodiments, the targeting component comprises a FLAG-tag and the effector components a poly-(8×) HIS-tag and a c-myc tag.

The methods of the invention envisage selecting single-cell clones which stably express the multiplexing scaffold proteins carrying the desired functional components. The term "clone" or "single-cell clone" refers to a group of identical cells that are derived from the same cell and can typically be obtained through serial dilution. The identification of single cell clones ensures the production of a homogenous product. While the selection as described herein may still generate clones that express different heteromultimers with varying ratios of functional components, it will allow to identify clones expressing molecular heteromultimers that are enriched in specific effector components, such that the relative number of multimers with the desired ratio of functional components produced by said clone is significantly increased.

In particular embodiments, more particularly where different functional components are used, further isolation steps are performed to identify molecular heteromultimers with the desired ratio of the different functional components.

The methods provided herein thus involve transfecting host cells with nucleic acids encoding multimerizing scaffold polypeptides which are lined to different functional components. More particularly, the methods typically involve transfecting a host cell, simultaneously or sequentially with a tracking component fused to a first multimerizing scaffold polypeptide, a second functional component fused to a second multimerizing component, a third functional component fused to a third functional component and so on. In particular embodiments of the methods provided herein, the host cells are transfected with a single vector carrying two different functional components. In other particular embodiments of the methods provided herein, the host cells are transfected simultaneously with two different functional components. For example, in particular embodiments, the nucleotide sequences encoding the third functional component fused to a third multimerizing scaffold polypeptide and the fourth functional component fused to a fourth multimerizing scaffold polypeptide are introduced simultaneously. In alternative embodiments of the methods provided herein the third functional component fused to a third multimerizing scaffold polypeptide and the fourth functional component fused to a fourth multimerizing scaffold polypeptide are transfected separately. In the latter case, an additional selection step can be added which offers the opportunity to first select the clones which express the previously introduced components more or less efficiently, depending on the desired ratio of functional components. For instance, in particular embodiments, it is determined after transfection which cells efficiently express the third functional component fused to a third multimerizing scaffold polypeptide such that these cells can be selected to be transfected with the fourth functional component in order to create cells expressing tetrafunctional heteromultimer protein complexes with the desired ratio of functional components, such as in that case a higher ratio of third functional components vs fourth functional components.

Accordingly, in particular embodiments, the methods according to present invention comprise, after the step of identifying clones which appropriately express bifunctional multimers as described in step (c) above, and in replacement of steps (d) to (f) above, the steps of (i) transfecting said clones with a nucleic acid vector that encodes a third functional component fused to a third multimerizing scaffold polypeptide;

(ii) expressing multimerizing polypeptides and allowing them to multimerize into multimers comprising a fixed number of one or more of said tracking components and comprising one or more of said second and third functional components;

(iii) selecting single-cell clones secreting multimers having the desired relative ratio of second and third functional components;

(iv) transfecting said clones with a nucleic acid vector that encodes a fourth functional component fused to a fourth multimerizing scaffold polypeptide;

(v) expressing the multimerizing polypeptides and allowing them to multimerize into multimers comprising a fixed number of one or more tracking components and one or more of said second, third and fourth functional component;

(vi) selecting single-cell clones secreting multimers having the desired relative ratio of second, third and fourth functional components; and (vii) optionally, repeating said steps of transfecting, expressing, and selecting for (X-4) functional components each fused to a multimerizing scaffold polypeptide, wherein the X is a natural number between 4 and 20 and is at most the total number of polypeptides present in the multimerizing scaffold. It should be clear to the skilled in the art, that in case a nucleic acid encodes more than one functional component, the naming of "Xth" functional component would follow logic numbering.

In particular embodiments, the methods according to present invention are used to generate heterofunctional multimers which comprise one or more targeting components and one or more effector components. In particular embodiments, the second functional component is a targeting component and the third and fourth, and optionally further and up to $X^{th}$ functional components are effector components, wherein X is a natural number between 4 and 20 and is at most the total number of polypeptides present in the multimerizing scaffold. Examples of envisaged targeting and effector components are described herein above.

In particular embodiments, the nucleic acid vector is a multicistronic vector encoding two or more functional components fused to a multimerizing scaffold polypeptide. The skilled person will understand that when using multicistronic vectors, the number of steps and nucleic acid vectors required to obtain single-cell clones secreting multimers having the desired relative ratio of second, third and fourth, and optionally, fifth, sixth, seventh or eighth, functional components decreases.

While multifunctional multimerizing scaffolds can be of interest, it can similarly be of interest to obtain bifunctional multimerizing scaffolds (e.g. one targeting and one effector function), with a well-defined ratio. In these embodiments, the multimer provides the advantage that several effector and targeting molecules are provided in one complex, which is beneficial to efficacy of both the targeting and effector function. The methods of the present invention allow stable production of such high-potency complexes.

The methods of the present invention are of particular interest in the generation of multifunctional heteromultimeric protein complex useful in the context of therapeutic methods, more particularly for targeting the immune system. For instance, the methods are of interest for generating heteromultimeric protein complexes which comprise different activators of the complement system, particularly the complement alternative pathway (CAP). Accordingly, in particular embodiments the methods involve preparing multifunctional heteromultimeric protein complexes with a defined ratio of the targeting and CAP-effector components within the multimer. These will be described more in detail below.

As indicated above, the host cell can be transfected with a single vector carrying two different functional components. In particular embodiments, the nucleic acid vector encodes two or more functional components, preferably two functional components, fused to one multimerizing scaffold polypeptide. In particular embodiments, if two functional components are fused to one multimerizing scaffold polypeptide, one of said two functional components is located upstream (i.e. toward the 5' end) of the multimerizing scaffold polypeptide, while the other is located downstream (i.e. toward the 3' end) of the multimerizing scaffold polypeptide.

A further aspect of the invention relates to the multifunctional heteromultimeric protein complexes obtainable by the methods described herein. In particular embodiments, these multimeric complexes are characterized in that they comprise a defined ratio of functional components. This can be of particular interest for certain applications. For instance, the inventors have found that in therapeutic methods targeting the immune system, the simultaneous delivery of more than one functional component, in addition to a targeting component which ensures targeted delivery, can have significant advantages. In particular embodiments, the multifunctional heteromultimeric components are characterized in that they comprise different effector components involved in immune activation. More particularly, the two or more effector components can be components which direct complement-dependent cytolysis and/or antibody-dependent cell-mediated cytotoxicity.

In more particular embodiments, multifunctional heteromultimeric protein complexes are provided, comprising two or more, preferably three or more, different functional components present in a defined relative ratio, of which one or more, preferably one, are tracking components. In more particular embodiments, the multifunctional heteromultimeric protein complex as described herein comprise at least four different functional components.

In certain applications of the multifunctional heteromultimeric protein complexes provided herein it might be favorable to be able to co-deliver different effector components which can lead to a synergistic therapeutic effect and/or to combine different targeting components which may increase the binding specificity and affinity and/or to direct one or more effector components to a target cell by use of both targeting and effector components. Hence, in particular embodiments, the multifunctional heteromultimeric protein complexes according to present invention comprise at least three different functional components. In alternative embodiments, the multifunctional heteromultimeric protein complexes comprise two different functional components, such as an effector and a target component.

The heteromultimeric proteins provided herein, can be characterized based on the valence of the one or more effector proteins. More particularly this is relevant where the number of different functional components is lower than the number of multimerizing scaffold polypeptides of the complex. For instance, where only one effector component is envisaged, it can be of interest to ensure that the valence of that effector component in the complex is as high as possible. In particular embodiments, the total number of functional components is 7 and the ratio of target to effector component is such that the valence of the effector component is at least 2, 3, 4, 5 or 6, preferably at least 3, most particularly 6.

As detailed herein, the valence of the effector components can be determined by measuring the signal of the effector component relative to the tracking component. For a given clone, this will represent an average of the effector valence.

The particular embodiments relating to the targeting, effector and tracking components as described above for the method for preparing multifunctional heteromultimeric protein complexes, also apply for the second aspect of present invention encompassing the multifunctional heteromultimeric protein complexes.

In particular embodiments, the multifunctional heteromultimeric protein complex according to present invention comprises one or more targeting components and one or more effector components. In more particular embodiments, the multifunctional heteromultimeric protein complex according to present invention comprises one or more targeting components and one or more effector components in addition to a tracking component.

In particular embodiments, the functional components are selected from the group comprising synthetic or natural peptides, biological macromolecules, polypeptides, proteins, peptide analogues, peptidomimetics, antibodies, antibody fragments and derivatives thereof.

In particular embodiments, the targeting component is selected from the group comprising antibodies, binding fragments thereof, ligands to a target cell receptor, and soluble receptors. In more particular embodiments, the targeting component is an antibody, or a binding fragment thereof or a cell-surface receptor ligand, more preferably wherein at least one of the targeting components is an antibody or a binding fragment thereof directed against a tumor antigen, against a surface marker of erythrocytes or against a pathogen-associated surface marker, even more preferably wherein at least one of the targeting components is multi-2D3 $V_HH$ anti-HER2 or scFv anti-GYPA.

In particular embodiments, the functional component is selected from the group comprising cytokines, growth factors, hormones, vaccine antigens, toxins, enzymes, self-antigens against which natural antibodies exist, antigenic cytoskeleton proteins, antigenic components, regulators of the complement system, antibodies or fragments or derivatives thereof (e.g. monomeric Fc, preferably monomeric Fc of IgG comprising the hinge and CH2 and CH3 domains of IgG).

The multifunctional heteromultimeric protein complexes according to present invention comprise multimerizing polypeptides, which act as a scaffold to join the different functional components. In particular embodiments, each functional component is fused to a multimerizing scaffold polypeptide. In particular embodiments, the multimerizing polypeptides are components of the C4bp protein. As detailed herein above, it is of particular interest to make use of both the alpha and beta chains of the C4bp protein, as this allows the introduction of a fixed number of tracking components in the multimer. Accordingly, in particular embodiments of the method of present invention, the tracking component is fused to the beta-chain of C4bp, preferably the c-terminal part of a beta-chain of C4bp. In particular embodiments of the method of present invention, each targeting component is fused to the alpha-chain of C4bp. In particular embodiments of the method of present invention, each effector component is fused to the alpha-chain of C4bp.

As also detailed herein above, the multimers provided herein are of particular interest where a particular ratio of functional components is of interest and/or where the homogeneity of the multimers is important. In particular embodiments the relative ratio of the tracking component, the targeting component and first and second effector components is 1:N:M, wherein N+M is preferably between 3 and 20, most particularly between 8 and 11, most particularly between 7 and 11, such as 7, 8, 9, 10 or 11. N refers to the number of targeting components and M refers to the number of effector components or vice versa and either of. N and M can be any number between 1 and 19. In particular embodiments, the invention provides multifunctional heteromultimeric protein complexes wherein the functional components comprise factors capable of modulating the complement system. More particularly, in particular embodiments, the functional components comprise a specific ratio of targeting and complement dependent cytolysis or complement alternative pathway (CAP) effector components. CAP effectors can ensure lysis of a target cell by activating the host CAP towards said target cell. The "complement alternative pathway" or "CAP" is an innate component of the immune system's natural defense against infections. The alternative pathway is one of three complement pathways that make cells more susceptible to the action of phagocytes and kill pathogens. The pathways differ in the manner in which they are triggered and ultimately generate a key enzyme called C3 convertase. The complement alternative pathway is activated when the generated-C3b protein directly binds an activator such as certain particulate polysaccharides, for example, bacterial (LPS), yeast (zymosan), or plant (inulin) polysaccharides, fungi, bacteria, viruses and certain mammalian cells. This leads to the assembly of C3 and C5 convertase on an activated plasma membrane, ultimately resulting in the formation of membrane attack complexes (MAC) through the oligomerization of C9 factor. This creates a hole or pore in the plasma membrane that can kill or damage the cell leading to cytolysis. Examples of effector components capable of activating the CAP includes positive regulators of the CAP or members of the complement system, such as for example, FHR4, Properdin factor, MBL-associated-serine-protease 3 (MASP-3) and P-selectin, preferably FHR4 or Properdin factor, most preferably FHR4. In particular embodiments, the specific ratio of CAP effector components over the targeting component is as high as possible.

In particular embodiments, the effector components comprise FHR4 and/or Properdin as effector components for CAP-activation. Indeed, the inventors have found that the multifunctional heteromultimeric protein complexes comprising FHR4 and/or Properdin as effector components added to a targeting component can ensure destructive cell targeting by directing the activation of the CAP towards target cells. Moreover, it was found that when both FHR4 and Properdin are present in the heteromultimer, the overall C3b deposition on the target cell by both molecules was enhanced. In particular embodiments, the targeting component is a component targeting cancer cells or erythrocytes. More particularly, present invention concerns tri- and tetrafunctional heteromultimers displaying (i) FHR4 and/or Properdin, preferably FHR4, as effector component for CAP-activation, combined with (ii) a targeting component, and (iii) a tracking component. Multifunctional heteromultimeric protein complexes displaying a high number of human FHR4 and/or Properdin effector components are of particular interest to promote enhanced C3b assembly and lysis of target cells. An increased stoichiometry of CAP-effector densities on target membrane surfaces promotes C3b assembly to levels allowing efficient CDC, overcoming complement inhibition threshold defined by mCRP densities on tumour cells and soluble factor H. The engineering of fusion recombinant multimeric CAP-effectors, combined to targeting components (such as a scFv or $V_HH$) that recognises target surface molecules, allows directing much higher local densities of positive regulators of CAP onto target membrane surfaces, organised as clusters.

In particular embodiments, FHR4 or Properdin is fused to the alpha-chain of C4bp.

In particular embodiments, the specific ratio of FHR4 or Properdin over the targeting component present in the multifunctional heteromultimeric protein complex is as high as possible.

In particular embodiments, the multifunctional heteromultimeric protein complexes as described herein comprise at least 3, preferably at least 6 FHR4 proteins.

In particular embodiments, if the multimerizing polypeptides are components of the C4bp protein complex, and if the tracking component is fused to the beta-chain of C4bp, the specific ratio of FHR4 or Properdin over the targeting component present in the multifunctional heteromultimeric protein complex is at least 3, at least 4, at least 5 or at least 6, preferably 3, 4, 5 or 6, more preferably 6, and/or the specific ratio of FHR4 or Properdin over the tracking component present in the multifunctional heteromultimeric protein complex is at least 3, at least 4, at least 5 or at least 6, preferably 3, 4, 5 or 6, more preferably 6.

In particular embodiments, if the multimerizing polypeptides are components of the C4bp protein complex, and if the tracking component is fused to the beta-chain of C4bp, the ratio of target to effector component is such that the valence of the effector component is at least 2, 3, 4, 5 or 6, preferably at least 3, most particularly 6. As detailed herein, the valence of the effector components can be determined by measuring the signal of the effector component relative to the tracking component. For a given clone, this will represent an average of the effector valence.

In particular embodiments, the invention provides multifunctional heteromultimeric protein complexes wherein the functional components comprise factors capable of activating antibody-dependent cell-mediated cytotoxicity (ADCC). Factors capable of activating ADCC can attract a natural killer (NK) cell and ensure lysis of a target cell by activating ADCC. The "antibody-dependent cell-mediated cytotoxicity" or "ADCC" is a mechanism of cell-mediated immune defense whereby an effector cell of the immune system, classically NK cells expressing Fc receptors (e.g. CD16 or FcγRIII), actively lyses a target cell, whose membrane-surface antigens have been bound by specific antibodies or fragments or derivatives thereof (e.g. Fc portion of an antibody such as IgG). ADCC is independent of the immune complement system.

In particular embodiments, the factor capable of activating antibody-dependent cell-mediated cytotoxicity (ADCC) comprises monomeric Fc, preferably monomeric Fc of IgG comprising the hinge and the CH2 and CH3 domain. In a more particular embodiment, the amount of monomeric Fc present in the multifunctional heteromultimeric protein complex is as high as possible, preferably sufficient to form at least 1, at least 2, at least 3 Fc dimers, more preferably sufficient to form at least 3 Fc dimers.

In particular embodiments, the specific ratio of monomeric Fc over the targeting component present in the multifunctional heteromultimeric protein complex is as high as possible.

In particular embodiments, if the multimerizing polypeptides are components of the C4bp protein complex, and if the tracking component is fused to the beta-chain of C4bp, the specific ratio of monomeric Fc over the tracking component present in the multifunctional heteromultimeric protein complex is at least 2, at least 3, at least 4, at least 5, at least 6 or at least 7, preferably an even number such as 2, 4 or 6, more preferably 6 or 7.

In particular embodiments, the targeting component in the multimers envisaged herein is an antibody, or a binding fragment thereof, directed against a tumor antigen.

Tumor antigens are molecules that are differentially expressed on a tumor cell compared to a normal cell. Tumor antigens are useful tumor markers for identifying tumor cells using diagnostic tests and are used for targeted cancer therapies. In some embodiments of the multimers envisaged herein, the tumor antigen is known or thought to contribute to a tumorigenic characteristic of the tumor cell. Numerous tumor antigens are known in the art. For example, alphafetoprotein, carcinoembryonic antigen, CA-125, MUC-1, epithelial tumor antigen, tyrosinase, melanoma-associated antigen, ras, p53, HER2/neu, FGF-5, EpCAM or STEAP1, CD19, CD20, preferably HER2/neu. Whether a molecule is a tumor antigen can be determined according to techniques and assays well known to those skilled in the art, such as for example clonogenic assays, transformation assays, in vitro or in vivo tumor formation assays, gel migration assays, gene knockout analysis, etc. In more particular embodiments of the multimers envisaged herein, the targeting component is multi-2D3 $V_HH$ anti-HER2. In particular embodiments, multi-2D3 $V_HH$ anti-HER2 is fused to the alpha-chain of C4bp.

In alternative embodiments, the multimers envisaged herein comprise a targeting component which binds to erythrocytes. Indeed, the inventors have shown that the complexes of the present invention can also effectively direct the complement system to other cells as illustrated herein with erythrocytes. In particular embodiments, the targeting component is an antibody or antibody binding fragment thereof directed against a surface marker of erythrocytes. For example, blood group antigen, CD71, CD35 or Glycophorin A (GYPA aka CD235a), preferably GYPA. In more particular embodiments, the targeting component is scFv anti-GYPA. In particular embodiments, scFv anti-GYPA is fused to the alpha-chain of C4bp.

The multifunctional heteromultimeric protein complexes of the present invention comprise one or more tracking components. The different options of tracking components are described herein above. The use of fluorescently tagged peptides as tracking components are particularly convenient for FACS analysis as they do not require the use of additional fluorescent tagged monoclonal antibodies. In particular embodiments of the present invention, the tracking component present in the multimers envisaged herein is a fluorescent protein, preferably eGFP. For therapeutic use in humans, where the presence of a fluorescent moiety may not be advisable, a proteolytic cleavage site can be introduced between the tags, the fluorescent protein and the scaffold protein to remove said tags or fluorescent protein after purification of the multimers. Example of such cleavage sites are well known in the art and include tobacco Etch virus (TEV) (Tyr-Xaa-Val-Gly-|-Gly, wherein '|' represents the peptide bond which will be cleaved), as are the methods to introduce them in the constructs of the invention or to use them for releasing protein moieties.

In particular embodiments, the present invention provides multifunctional heteromultimeric protein complexes wherein the functional components comprise factors capable of simultaneously directing complement-dependent cytolysis and antibody-dependent cell-mediated cytotoxicity.

In particular embodiments, the present invention provides multifunctional heteromultimeric protein complexes displaying at least (i) FHR4 and/or Properdin, (ii) monomeric Fc, (iii) a targeting component, and (iv) a tracking component.

In more particular embodiments, the present invention provides tetra- and penta-functional heteromultimers displaying (i) FHR4 and/or Properdin, (ii) monomeric Fc, (iii) a targeting component, and (iv) a tracking component. Multifunctional heteromultimeric protein complexes displaying a high number of FHR4 and/or Properdin effector components and a high number of monomeric Fc are of particular interest to promote simultaneously complement-dependent cytolysis and antibody-dependent cell-mediated cytotoxicity (ADCC).

In particular embodiments, if the multimerizing polypeptides comprise the C4bp protein complex as the multimerizing scaffold, and if the tracking component is fused to the beta-chain of C4bp, the specific ratio of FHR4 or Properdin over the tracking component present in the multifunctional heteromultimeric protein complex is preferably at least 3, at least 4, at least 5 or at least 6, more preferably 3, 4, 5 or 6, most preferably 6, and the specific ratio of monomeric Fc over the tracking component present in the multifunctional heteromultimeric protein complex is preferably at least 3, at least 4, at least 5, at least 6 or at least 7, more preferably an even number such as 2, 4 or 6, most preferably 6 or 7.

Such ratios of FHR4 or Properdin and monomeric Fc over the tracking component present in the multifunctional heteromultimeric protein complex can be achieved by using one or more nucleic acid vectors encoding two or more functional components fused to one multimerizing scaffold polypeptide.

In particular embodiments, a specific ratio of FHR4 or Properdin over the tracking component present in the multifunctional heteromultimeric protein complex is preferably at least 3, at least 4, at least 5 or at least 6, more preferably 3, 4, 5 or 6, most preferably 6, and a specific ratio of monomeric Fc over the tracking component present in the multifunctional heteromultimeric protein complex is preferably at least 3, at least 4, at least 5, at least 6 or at least 7. More preferably, a specific ratio of monomeric Fc over the tracking component includes an even number such as 2, 4 or 6. Most preferably the number of monomeric Fc in the multifunctional heteromultimeric protein complex is 7, which is achieved by the method for preparing multifunctional heteromultimeric protein complexes with a defined ratio of functional components as described herein; wherein in step (a) a tracking component is fused to the beta-chain of C4bp and a targeting component and monomeric Fc are fused to the alpha-chain of C4bp, preferably the targeting component is fused to the 5' end of the alpha-chain of C4bp and monomeric Fc is fused to the 3' end of the alpha-chain of C4bp; wherein in step (b) the multimerizing scaffold peptides multimerize into trifunctional multimers comprising one tracking component, 7 targeting components and 7 monomeric Fc's; wherein in step (c) single-cell clones are selected that secrete the trifunctional multimers; wherein in step (d) said clones are transfected with a nucleic acid vector that encodes FHR4 or Properdin and monomeric Fc fused to the alpha-chain of C4bp; wherein in step (e) the multimerizing scaffold polypeptides are expressed and allowed to multimerize into multimers comprising one tracking component, at least one targeting component, at least one FHR4 or Properdin component and at least two monomeric Fc components; wherein in step (f) single-cell clones secreting multimers having the desired relative ratio of FHR4 or Properdin and monomeric Fc are selected, preferably the single-cell clones secreting multimers having one tracking component, one targeting component, at least 3 FHR4 or Properdin components and at least 2 monomeric Fc components are selected; and wherein in step (g) said clones the produced multimeric protein complexes are recovered.

When at least 2 monomeric Fc components are present in the heteromultimeric protein complex, the monomeric Fc components may dimerize.

In more particular embodiments, the present invention provides tetra- and penta-functional heteromultimers displaying (i) at least 3, preferably at least 6, components comprising a FHR4 or Properdin protein fused to the alpha-chain of C4bp, (ii) at least 2, preferably at least 6, components comprising a monomeric Fc fused to the alpha-chain of C4bp, (iii) one targeting component fused to the alpha-chain of C4bp, and (iv) one tracking component fused to the beta-chain of C4bp. In particular embodiments, the alpha-chain of C4bp is fused to two functional components. For example, the FHR4 or Properdin protein is located upstream of the alpha-chain of C4bp and monomeric Fc is located downstream of the alpha-chain of C4bp and/or the targeting component is located upstream of the alpha-chain of C4bp and monomeric Fc is located downstream of the alpha-chain of C4bp.

The invention further relates to the use of the multifunctional heteromultimeric protein complexes according to the invention in therapy. More particularly, the multifunctional heteromultimeric protein complexes described herein comprising effectors components for CAP and/or ADCC activation can be used in the prevention and/or treatment of diseases or conditions which would benefit from an enhanced lysis of target cells, such as in cancer.

The skilled person will understand that the disease or condition which could be prevented and/or treated by multifunctional heteromultimeric protein complexes according to the invention mainly depends on which targeting components are comprised within the multifunctional heteromultimeric protein complexes.

Accordingly, present invention provides a multifunctional heteromultimeric complex as described herein for use in the treatment of cancer. Examples of cancer include but are not limited to, carcinoma, lymphoma (e.g., non-Hodgkin's lymphoma, chronical lymphocytic leukaemia), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulvar cancer, thyroid cancer, hepatic carcinoma and various types of head and neck cancer. Likewise, the present invention provides also methods for the treatment of cancer comprising administering to a subject in need thereof a therapeutically effective amount of a multifunctional heteromultimeric protein as described herein. In view of the above, present invention also provides the use of a multifunctional heteromultimeric complex as described herein in immunotherapy and to methods for immunotherapy comprising administering to a subject an therapeutically effective amount of a multifunctional heteromultimeric complex as described herein.

As used herein, a phrase such as "a subject in need of treatment" includes subjects that would benefit from treatment of a recited disease or disorder. Such subjects may include, without limitation, those that have been diagnosed with said disease or disorder, those prone to contract or develop said disease or disorder and/or those in whom said disease or disorder is to be prevented.

The terms "subject" and "patient" are used interchangeably herein and refer to animals, preferably vertebrates, more preferably mammals, and specifically include human patients and non-human mammals. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients or subjects are human subjects.

A 'therapeutic amount' or 'therapeutically effective amount' as used herein refers to the amount of multifunctional heteromultimeric complex effective to treat a disease or disorder in a subject, i.e., to obtain a desired local or systemic effect. The term thus refers to the quantity of multifunctional heteromultimeric complex that elicits the biological or medicinal response in a tissue, system, animal, or human that is being sought by a researcher, veterinarian, medical doctor or other clinician. Such amount will typically depend on the multifunctional heteromultimeric complex and the severity of the disease, but can be decided by the skilled person, possibly through routine experimentation.

In particular embodiments, when at least one of the targeting components of the multifunctional heteromultimeric complex is an antibody or fragment thereof directed against tumor-associated antigen HER2/neu (e.g. multi-2D3 $V_HH$ anti-HER2), the preferred type of cancer to be treated with said multifunctional heteromultimeric complex is breast cancer, more preferably HER2-positive breast cancer.

One of the main challenges of the complement-dependent immunotherapies is the necessity to overcome a given threshold for complement activation on plasma membrane surfaces that is established by host complement inhibitors. These complement inhibitors are either soluble, such as factor H and C4bp, or membrane-anchored, such as membrane-associated complement regulatory proteins (mCRPs) such as CD35 (CR1 or complement receptor type 1), CD46 (MCP or membrane cofactor protein), CD55 (DAF or decay accelerating factor), or CD59 (MIRL or membrane inhibitor of reactive lysis). One or more mCRPs are generally upregulated in tumour cells. The presence of overexpressed mCRPs on tumours enhances their protection from the host immune system, and consequently raises the complement inhibition threshold (CIT). Since the complement homeostasis is the result of a steady-state between positive and negative complement regulators, enhancing the density of negative regulators on tumour cell plasma membrane surfaces leads to a shift of the complement metastable equilibrium towards enhanced inhibition. Overcoming this threshold means bringing increased local concentrations of positive regulators of the complement to shift the complement steady-state towards activation. Consequently, antibodies are generally not capable of overcoming this elevated threshold for an efficient complement activation. The use of recombinant natural positive regulators of the complement alternative pathway (PRCAP) expressed as multimeric multifunctional molecules that are coupled to targeting functions is a key technology to increase the local stoichiometry of positive regulators of the complement alternative pathway (PR-CAPs), leading to the overwhelming of mCRP at tumour cell surface through an excessive directed CAP-activation. Known PRCAP include Properdin factor (2), and factor H-related protein 4 (FHR4) (4), MBL-associated-serine-protease 3 (MASP-3) (7) and P-selectin.

One of the drawbacks of most of therapeutic antibodies is the lack of CDC. FcγR binds to the top of the Fc region of IgG1 close to the hinge, in the CH2 domain that includes amino acids $Glu^{318}$, $Lys^{320}$ and $Lys^{322}$. The carbohydrate attached to the conserved glycosylation residue $Asn^{297}$ on Fc, responsible for the Fc dimer formation, stabilises the conformation of the receptor-binding epitope on Fc. Moreover, a hingeless IgG1 antibody has been shown to be unable to bind or activate C1q (9). Thus, C1q and FcγR binding to Fc takes place in the same region of CH2. This means that when ADCC takes place, the activation of the complement classical pathway through C1q binding cannot take place. Multimeric systems capable of directly activating complement alternative pathway (CAP) would lead to a selective and local enhancement of the activation of the C3b amplification loop not regulated by upstream C4bp and C1-INH of CCP. In addition, they would present the advantage to allow ADCC and CDC to simultaneously take place in contrast to conventional therapeutic Abs where ADCC engagement excludes CDC. More particularly, multifunctional heteromultimeric protein complexes displaying (i) a high amount of FHR4 and/or Properdin components and a high amount of (ii) monomeric Fc components, preferably an amount of monomeric Fc components capable of forming Fc dimers, have the advantage to trigger ADCC and CDC at the same time, through Fc fragments and FHR4 and/or Properdin moieties, in contrast to conventional IgGs. In particular embodiments, if the multimerizing polypeptides comprise the C4bp protein complex as the multimerizing scaffold, and if the tracking component is fused to the beta-chain of C4bp, such high amounts of FHR4 or Properdin components can be expressed as a specific ratio of FHR4 or Properdin over the tracking component present of at least 3, at least 4, at least 5 or at least 6, more preferably 3, 4, 5 or 6, most preferably 6, such high amounts of monomeric Fc components can be expressed as a specific ratio of monomeric Fc over the tracking component of at least 3, at least 4, at least 5, at least 6 or at least 7, more preferably an even number such as 2, 4 or 6, most preferably 6 or 7.

Another therapeutic application of particular interest is the destruction of Rhesus D erythrocytes as it is a source of foetus-mother incompatibility. Other appropriate applications include, without limitation, transplant recipients (e.g., bone marrow, heart, kidney, liver, pancreas, and lung) where the protein construct is delivered, for example, to T cells, thereby resulting in the death of a substantial number, if not all, of the T cells.

Other possible applications include a variety of autoimmune or infectious diseases involving an intracellular microorganism (e.g., *Mycobacterium tuberculosis, Salmonella*, influenza virus, measles virus, hepatitis B virus, hepatitis C virus, human immunodeficiency virus, HIV and *Plasmodium falciparum*). Accordingly, present invention also provides a multifunctional heteromultimeric complex as described herein for use in the treatment of an autoimmune disease or infectious disease involving an intracellular microorganism, preferably said infectious disease involving an intracellular microorganism is selected from tuberculosis, gonorrhea infection, cystic fibrosis, *Borrelia* infection, *Plasmodium falciparum* infection, Haemophilius infection, *Staphylococcus* infection, *Salmonella* infection, *Yersinia* infection, influenza, measles, hepatitis B, hepatitis C, HIV, leptospirosis, Lemierre's syndrome and meningitis and other forms of meningococcal disease and, and infections caused by multi drug resistant bacteria, more preferably said infectious disease involving an intracellular microorganism is HIV; and also methods of treating a patient suffering from an autoimmune disease or infectious disease involving an intracellular microorganism comprising administering to said subject a therapeutically effective amount of a multifunctional heteromultimeric complex as described herein, wherein said infectious disease involving an intracellular microorganism is preferably selected from tuberculosis, gonorrhea infection, cystic fibrosis, *Borrelia* infection, *Plasmodium falciparum* infection, Haemophilius infection, *Staphylococcus* infection, *Salmonella* infection, *Yersinia* infection, influenza, measles, hepatitis B, hepatitis C, HIV, leptospirosis, Lemierre's syndrome and meningitis and other forms of meningococcal disease and, and infections caused by multi drug resistant bacteria, more preferably said infectious disease involving an intracellular microorganism is HIV.

In the case of infections, the multifunctional heteromultimeric protein complexes are delivered to the infected cells by targeting specific pathogen-associated markers, thereby resulting in the death of a substantial number of, in not all, the cells and thus a substantial decrease in the number of, if not total elimination of, the microorganisms. For instance, the multifunctional heteromultimeric protein complexes can be used to overcome viral infections. For example, multimers with an anchoring system against gp120 HIV Env (e.g. scFv or $V_HH$ anti-gp120 or anti-gp41, whole soluble or D1 D2 of CD4) against can target HIV-infected cells that express gp120 at their surfaces. Multimers can directly bind circulating HIV virions and lead to CAP activation. It has been shown that complement is active towards HIV, but not efficiently and fast enough to be able to establish an efficient innate immune response. Moreover, C3b breakdown products on opsonised virus surfaces can be used to the advantage of the virus, and be captured by CD11b (CR3) and CD11c (CR4) receptors on host phagocytes, such as dendritic cells or macrophages. Enhancing host complement activation on HIV with the multifunctional heteromultimeric protein complexes can modulate efficiently the host complement activation towards the virus.

In autoimmune diseases, the multifunctional heteromultimeric protein complexes can contain a targeting moiety directed at the T cells ($CD4^+$ and/or $CD8^+$) and/or B cells capable of producing antibodies that are involved in the tissue destructive immune responses of the diseases.

For treatment of infectious diseases caused by bacteria and fungi, and since bacteria and fungi do not express mCRPs, the FHR4-based multimers as described herein should be particularly efficient towards such microorganisms. An example is the possibility to design the scFv derived from Panobacumab (a human pentameric IgM antibody with a mouse J chain) to target LPO-O-polysaccharide of *P. Aeruginosa*.

Furthermore, many microorganisms, especially bacteria that are multi-resistant against antibiotics (MDR: multi drug resistant), are capable of binding the host soluble factor H, thus escaping complement-mediated inactivation. FHR4-based multimers as described herein targeting these microorganisms through binding to the surface molecule that normally binds to factor H, would lead to a strong complement activation.

A non-limiting list of bacteria that bind factor H (between brackets is the surface molecule binding to factor H):

*Neisseria gonorrhoeae* (PorB 1A) responsible for gonorrhea infection,

*Pseudomonas aeruginosa* (Tuf) responsible for cystic fibrosis,

*Borrelia* transmitted by ticks & lice & lyme,

*Leptospira interrogans* (LfhA) infection known as leptospirosis,

*Haemophilus influenzae*, gram-negative coccobacillary, responsible for a wide range of localized and invasive infections,

*Fusobacterium necrophorum* (Sbi), responsible for lemierre's syndrome,

*Staphylococcus aureus* (Sbi), antibiotic-resistant strains,

*N. meningitidis* (Fhbp) responsible for meningitis and other forms of meningococcal diseases,

*Y enterocolitica* (Ail, Yad all fH) responsible for yersinosis, and *S pneumoniae* (PspC, Hic).

Figure 1:
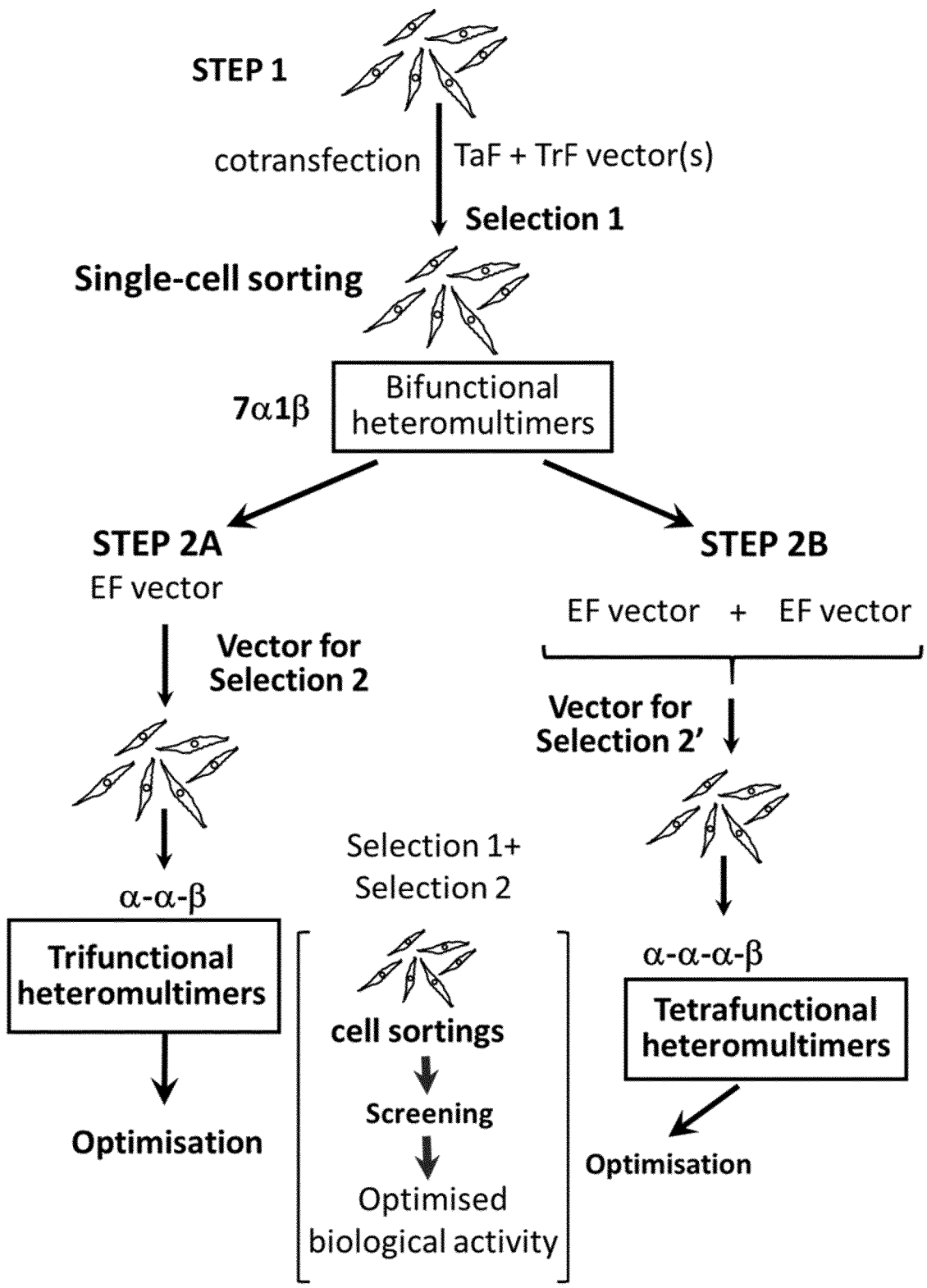
FIG. 1: Step-by-step generation of bi-, tri- and tetrafunctional multimeric immuno-conjugates.
Figure 2:
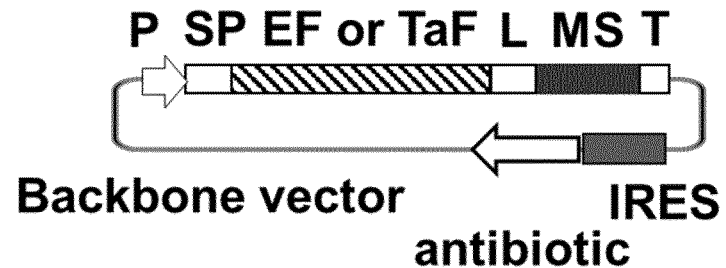
Figure 2:
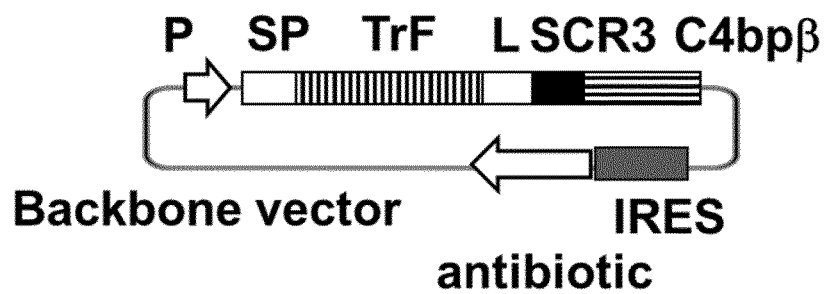
Figure 2:
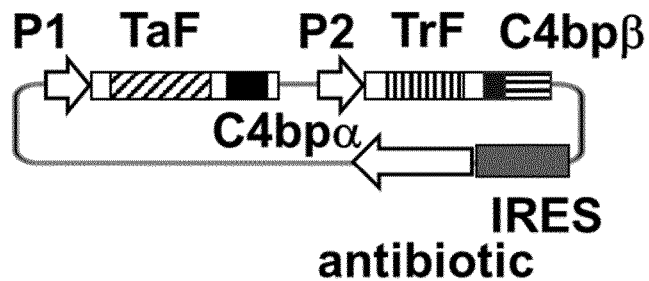
Figure 2:
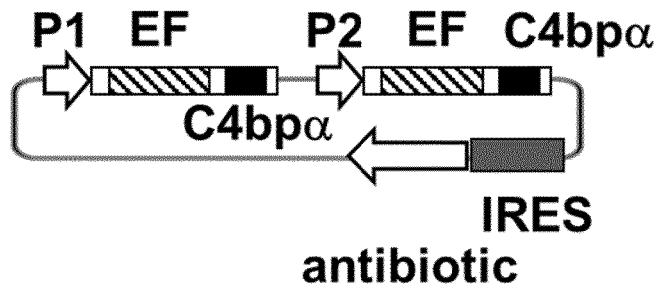

In view of the limitless amount of possible combinations of functional components, the multifunctional heteromultimeric protein complexes according to present invention can be used for multiple therapeutic applications. More particularly, the multimers provided herein are of interest in therapeutic applications which involve cell targeting. For example, drug delivery, cell removal, cell targeting, cancer therapy, and immunotherapy. In addition, the multimers of the present invention are of interest for use in medical imaging. The ability to obtain multifunctional heteromultimeric protein complexes which allow both targeting and a desired ratio of effector components increases the therapeutic effect and treatment specificity and decreases the possible side effects.

Present invention also encompasses pharmaceutical compositions comprising the multifunctional heteromultimeric protein complex according to present invention, in association with a pharmaceutically acceptable carrier. "Pharmaceutically acceptable" refers to approved or approvable by a regulatory agency of a certain country in which the molecule is put on the market. "Pharmaceutically acceptable carrier" refers to a pharmaceutically acceptable diluent, adjuvant, excipient, or vehicle. For example, phosphate buffered saline (PBS).

The invention further relates to the use of the multifunctional heteromultimeric protein complexes in screening methods. Indeed, the multimers of the present invention can be used as effectors in vitro, which allow for screening of factors which can influence processes activated or inhibited by the effectors.

The present invention is further illustrated in the following non-limiting examples.

EXAMPLES

Example 1

To study in vitro the relationship between the CAP-effector densities on targets and the efficacy of C3b activation and subsequent CDC, human erythrocytes were targeted as a proof-of-concept model: erythrocyte lysis assay represents an advantageous bioassay to measure CDC and subsequent lytic response photometrically by the amount of released hemoglobin. The technology has been further adapted to a model of cancer by replacing the targeting system to target Her2 tumour-associated antigen in Her2-overexpressing tumour cells. The principle of design and generation of the lead immuno-conjugates is the same in both erythrocyte and Her2-tumour models.

I) Material & Methods

All standard techniques not specifically described hereunder are well known in the art and can be found in current protocol manuals (e.g. Current Protocols in Molecular Biology).

Cells and Reagents

All the multimers were generated from stable transfected HEK-293 cells (ATCC CRL -1573). The clone number of the mouse anti-human FHR4 IgG1 mAb is #640212. The clone number of the unconjugated or PE-conjugated mouse anti-human C3/C3b/iC3b IgG1 mAb is 7C12. The polyclonal rabbit anti-human C3d Ab was purchased from DAKO. The clone number of the mouse anti-human Properdin IgG1 mAb is 1005. SK-BR-3 (HTB-30), BT474 (HTB-20) SK-OV-3 cells (HTB-77) were purchased from ATCC. U1 cells are U937 HIV-1 latently infected cells.

Gene Synthesis and Cloning

Backbone Expression Vector:

Expression vectors designed for the expression of the heteromultimeric proteins according to an embodiment of the invention. The backbone vector is any suitable vector for stable expression of recombinant functional components in mammalian cells. As an example, the vector used to express the recombinant multimeric glycoproteins is the pEF-IRE-Spac bi-cistronic vector. The different cassettes are spanned between restriction sites present in the pEF-IRESpac multiple cloning site (MCS). The MCS is followed by an IRES and the puromycin resistance gene. For each function, cDNA encoding (i) the R18 scFv anti-Glycophorin A (GYPA) (about 750 bp) (5) or (ii) the 2D3 $V_H$H anti-Her2 (patent WO2008068280) (about 384 bp), or (iii) human Properdin (about 1340 bp, Ref. UniProt n° P27918) or (iv) the human FHR4A (about 1680 bp, Ref. UniProt n° Q92496) lacking their signal peptides, or (v) the eGFP, were synthetized. All the synthetized genes, spanned between the restriction sites Bgl2 and BspE1, were further cloned into the appropriate cassette vectors. Properdin and FHR4 genes were cloned in the EF cassette vector displaying a His tag (FIG. 2 a), whereas eGFP was cloned into the TrF cassette vector (FIG. 2 *b*). TaF functions (scFv anti-GYPA, $V_H$H anti-Her2) were cloned either into (i) the EF cassette vector—displaying a His tag for purification—to generate final bifunctional heteromultimers used as control multimers, or (ii) into the TaF cassette vector—displaying a FLAG tag—to generate intermediate bifunctional heteromultimers whose producing cells are destined to further generate tri- and/or tetrafunctional heteromultimers (FIG. 2 *a*). In the latter case, His tag for purification of the said tri- or tetrafunctional heteromultimers is found in the effector function within heteromultimers.

Production of Bifunctional Heteromultimers in HEK293 Cells (FIG. 1)

Step 1

HEK293 cells were co-transfected with Taf (e.g. R18 scFv anti-GYPA to target erythrocytes or 2D3 $V_H$H anti-Her2 to target Her2-expressing tumour cells) and TrF expression vectors (e.g. eGFP). Transfected cells were selected using puromycin. Resistant cell clones were further isolated and cultured separately. Bifunctional heteromultimer-containing crude supernatants from single isolated clones were tested on erythrocytes or BT474 breast tumour cells, respectively. Multimer-loaded target cells were then stained with an anti-FLAG Ab and then analysed using flow cytometry. A single cell clone expressing high amount of bifunctional heteromultimers was expanded for further use.

Production of Tri-/Tetrafunctional Heteromultimers in HEK293 Cells (FIG. 1)

Step 2A: Production of Trifunctional Heteromultimers

Target Erythrocytes

Figure 3:
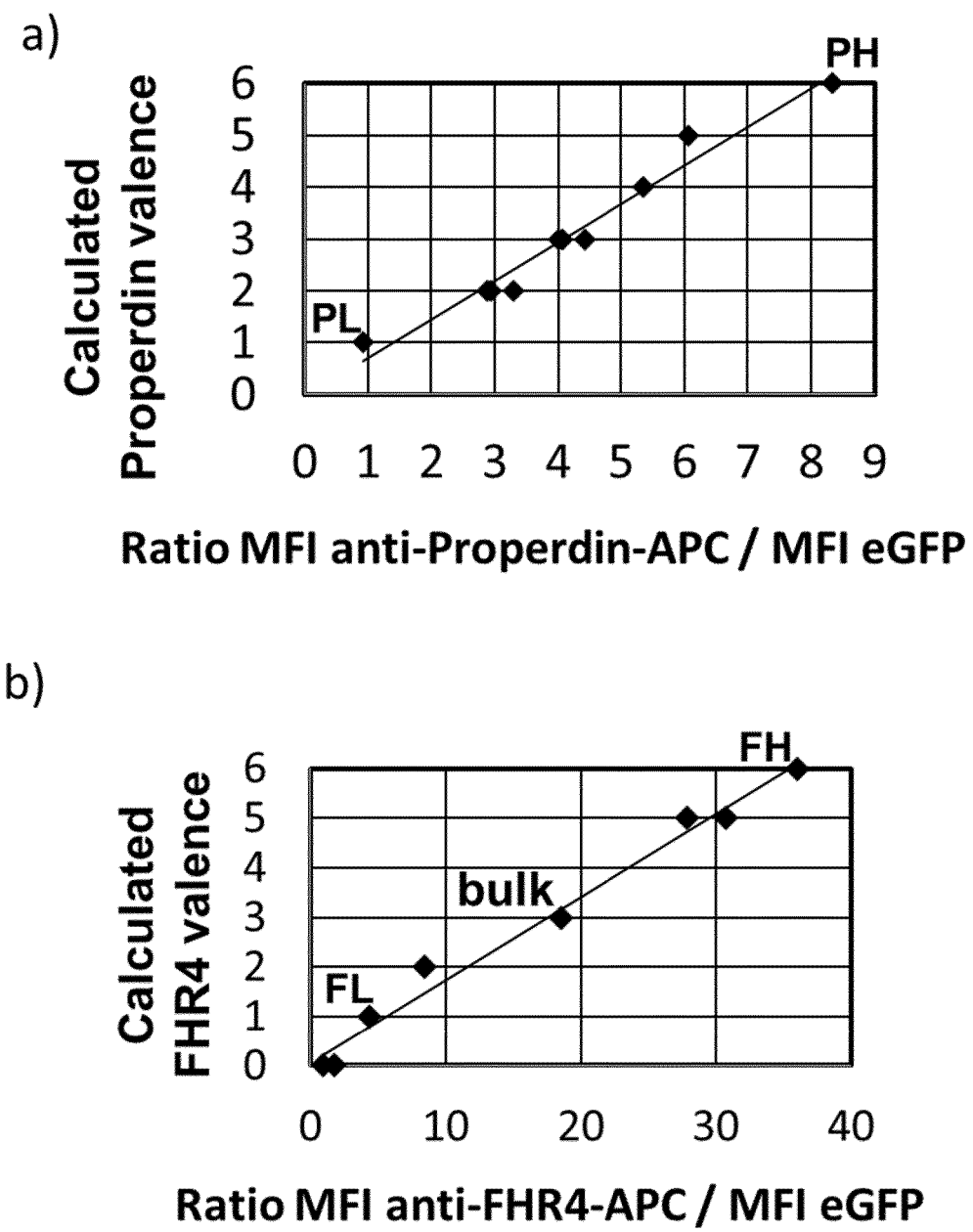

Multi-scFv anti-GYPA/mono-eGFP bifunctional heteromultimer-expressing cells were co-transfected with the EF cassette vectors, containing Properdin or FHR4 effector functions. Transfected cells were selected using puromycin and hygromycin. Resistant cell clones were isolated and cultured separately. Trifunctional heteromultimer-containing crude supernatants from single isolated clones were individually tested on erythrocytes. Multimer-loaded erythrocytes were then stained with a mouse anti-Properdin or anti-FHR4 mAbs, depending on the EF construct used, and then with an anti-mouse IgG Ab conjugated with a fluorochrome. Cells were analysed by flow cytometry. Mean fluorescence intensities (MFI) for Properdin or FHR4 and eGFP were measured for each supernatant, and ratios MFI Properdin/MFI eGFP or MFI FHR4/MFI eGFP were calculated to select clones with the lowest and highest ratios (FIG. 3 a & b).

Target Her2-Expressing Breast Tumor Cells

Multi-$V_HH$ anti-Her2/mono-eGFP bifunctional heteromultimer-expressing cells were co-transfected with the EF cassette vectors containing FHR4 effector function. The protocol to generate high FHR4-valence trifunctional heteromultimers is the same as described above using B474 breast tumour cells as target cells.

Step 2B: Production of Tetrafunctional Heteromultimers

Target Erythrocytes or Her2-Expressing Tumour Cells

Bifunctional heteromultimer-expressing HEK293 cells from Step 1 (with the multi-scFv anti-GYPA or the multi-$V_HH$ anti-Her2 targeting moieties) were co-transfected with the EF cassette vectors containing FHR4 and properdin PRCAP effectors and pTK-Hygro. Transfected cells were selected using puromycin and Hygromycin. Resistant cell clones were isolated and cultured separately. Tetrafunctional heteromultimer-containing crude supernatants from single isolated clones were sequentially individually screened on erythrocytes or Her2-expressing cells and analysed by flow cytometry for:

Ratios MFI His/MFI eGFP (following a staining with an anti-HIS Ab),

Multimers with High His/eGFP ratios were further tested for concomitant FHR4/Properdin expression (following a separate staining with anti-FHR4 or anti-Properdin mAbs). MFI Properdin/eGFP & MFI FHR4/MFI eGFP were calculated Multimers with High His/eGFP ratios and positive for Properdin and FHR4 were further tested on target cells for their ability to direct C3b depositions (following a staining with an anti-C3b mAb).

Multimer-expressing HEK293 cells were expanded in culture for further His-Trap purification.

Purification was performed using a FPLC His-Trap chromatography. Purified multimers were quantified by ELISA. The capture antibody coated to the ELISA plates was a rabbit anti-His pAb. The detection antibody was the 2F12 mouse anti-C4bp C-terminal α-chain mAb.

Figure 4:
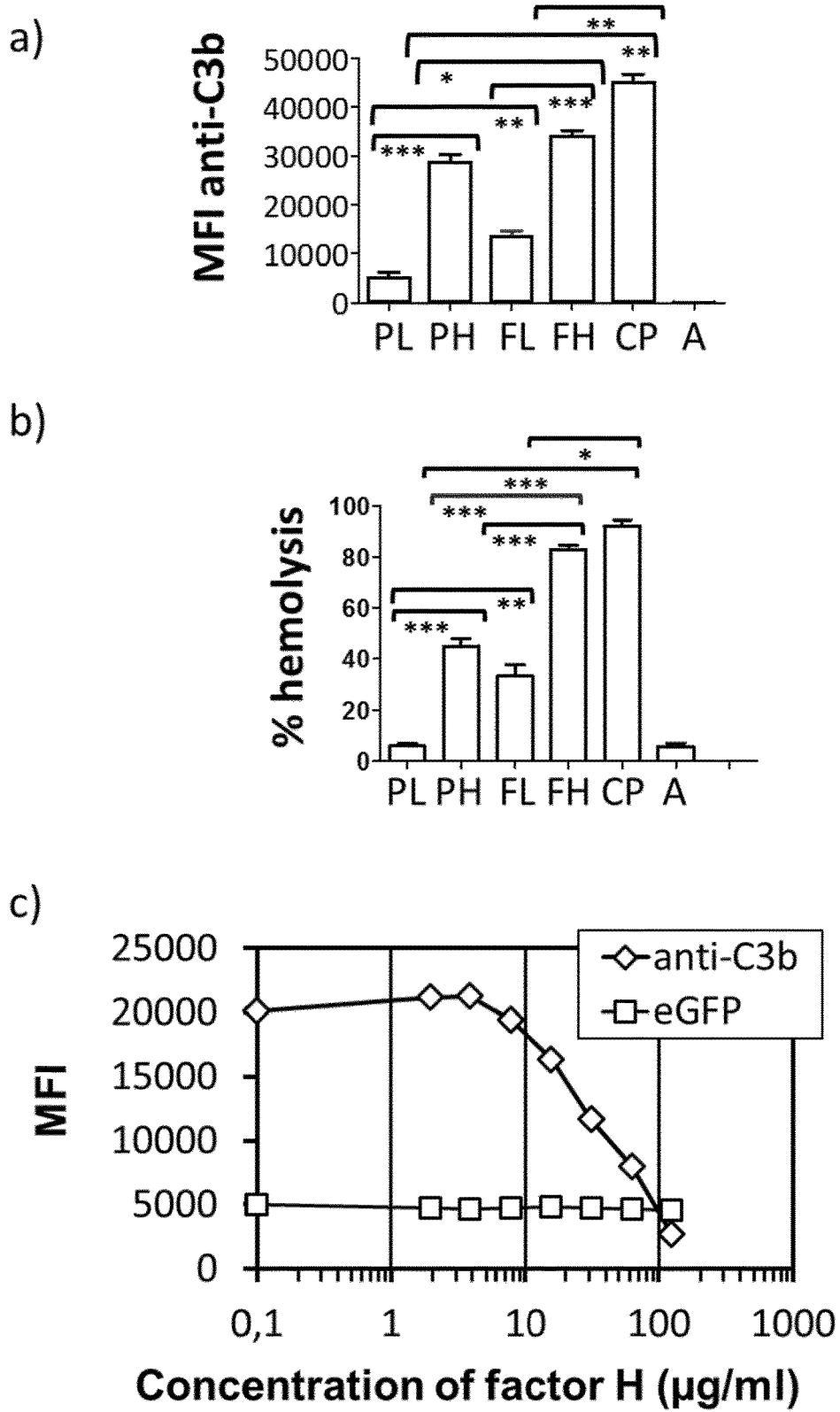

Relationship Between PRCAP Valence within Multimers, Opsonisation and Hemolysis Efficacy in the Erythrocyte Target Model (FIG. 4).

a) In order to test the multimer-directed C3b assembly on target erythrocytes, C5-deficient serum from an N donor was used as source of complement, as well as erythrocytes from an ABO-compatible healthy donor. Between 60 and 100 nMoL of purified multimers (PL, PH, FL, FH, CP, A)—representing saturating concentrations—were individually incubated in triplicate with erythrocytes in veronal buffer supplemented with C5-deficient human serum. Erythrocytes were then stained with a mouse anti-C3b mAb and anti-mouse IgG conjugated with APC. MFI for C3b were measured using flow cytometry.

b) Multimer-directed CDC assay was performed in the same experimental conditions, but using erythrocytes and autologous normal human serum (NHS) and hemoglobin release in the supernatants was measured. As positive control, erythrocytes were incubated in water. Spontaneous lysis corresponds to erythrocytes incubated with NHS in absence of multimers. Percentage of hemolysis was expressed according to the following formula: [(Sample OD−OD spontaneous lysis)/(OD 100% lysis−OD spontaneous lysis)]× 100. The average percentage of hemolysis and standard deviations of the triplicates for each multimer used were calculated. c) Factor H-mediated dose-response inhibition of opsonisation of FHR4-loaded erythrocytes. Erythrocytes (K) were incubated with about 100 nM purified high FHR4 valence trifunctional heteromultimers in veronal buffer supplemented with C5-deficient serum (K) and serial dilutions of soluble factor H (from about 0.1 to about 180 µg/ml). Erythrocytes were then stained with a mouse anti-human C3/C3b/iC3b mAb, and a secondary anti-mouse Ab conjugated with APC and analysed by flow cytometry. MFI for eGFP represented the multimer-densities on erythrocytes (squares), whereas MFI for APC (lozenges) represents levels of C3/C3b/iC3b assembly on erythrocytes.

Figure 5:
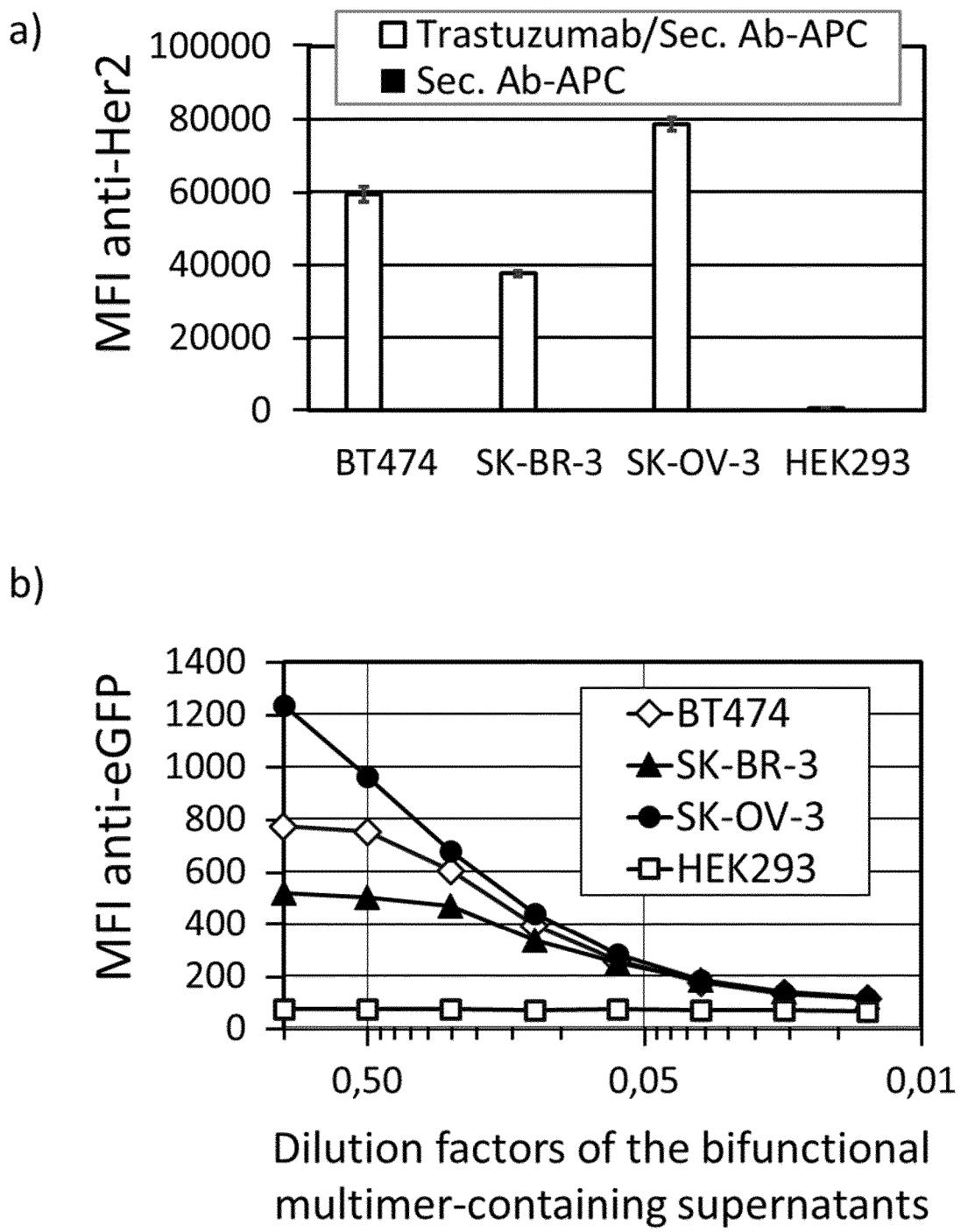

Analysis by Flow Cytometry of the Binding of the 2D3 $V_HH$ Anti-Her2/eGFP Bifunctional Heteromultimer on Three Her2-Overexpressing Breast Tumor Cell Lines (FIG. 5)

a) Comparative determination of the relative Her2-expression on BT474, SK-BR-3 and SK-OV-3 tumour cell lines. BT474, SK-BR-3, SK-OV-3 and control HEK293 were stained with the anti-HER2 antibody Trastuzumab and then an anti-human IgG Ab conjugated with APC Cells were analysed by flow cytometry and MFI for APC were determined.

b) In vitro analysis of the dose-response binding of the bifunctional heteromultimers on BT474, SK-BR-3, SK-OV-3 and control HEK293 cells. Serial dilutions of the previously selected bifunctional multi-2D3 $V_HH$ anti-Her2/mono-eGFP heteromultimer-containing supernatants were incubated with BT474, SK-BR-3, SK-OV-3 and control HEK293 cells. Multimer-loaded cells were then directly analysed by flow cytometry by measuring the MFI for eGFP.

Figure 6A:
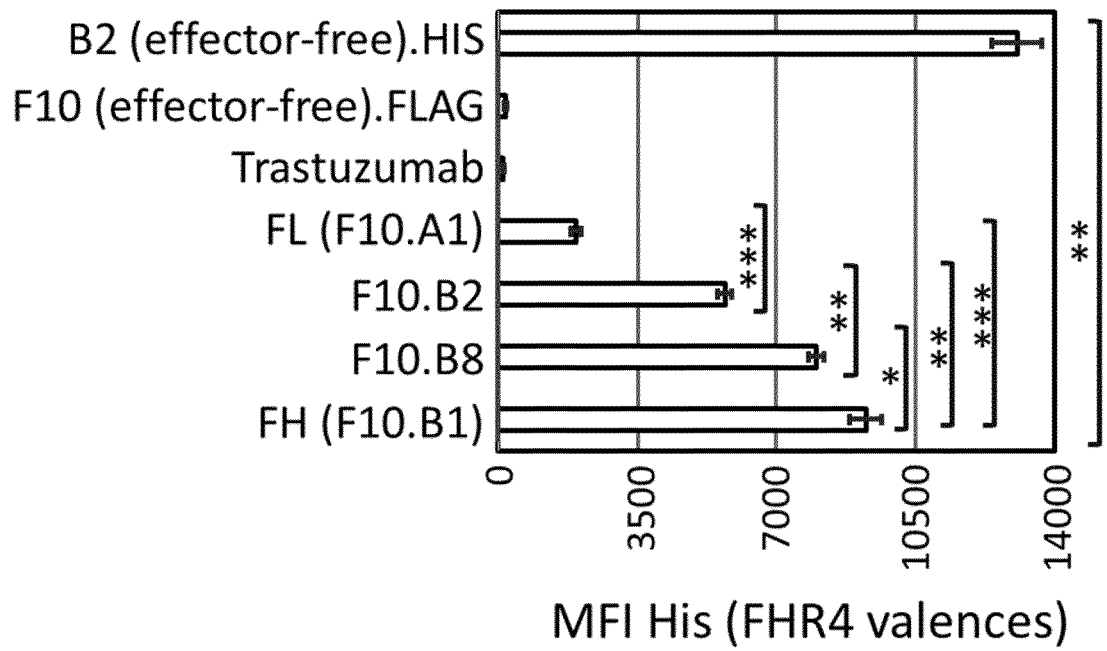
Figure 6B:
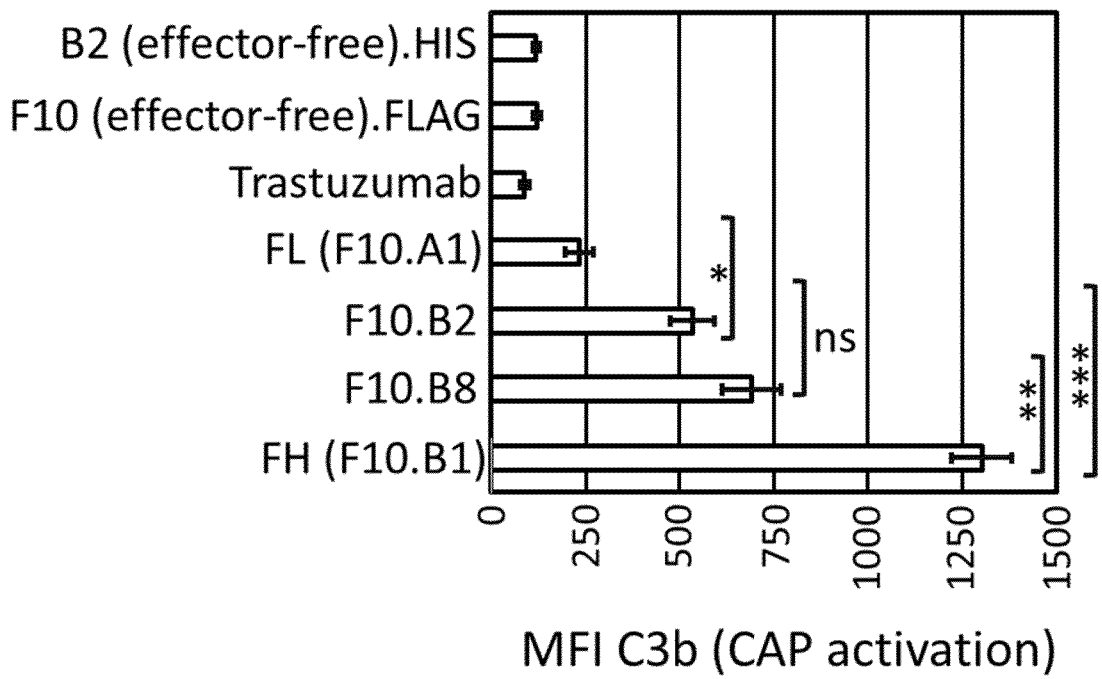
Figure 6C:
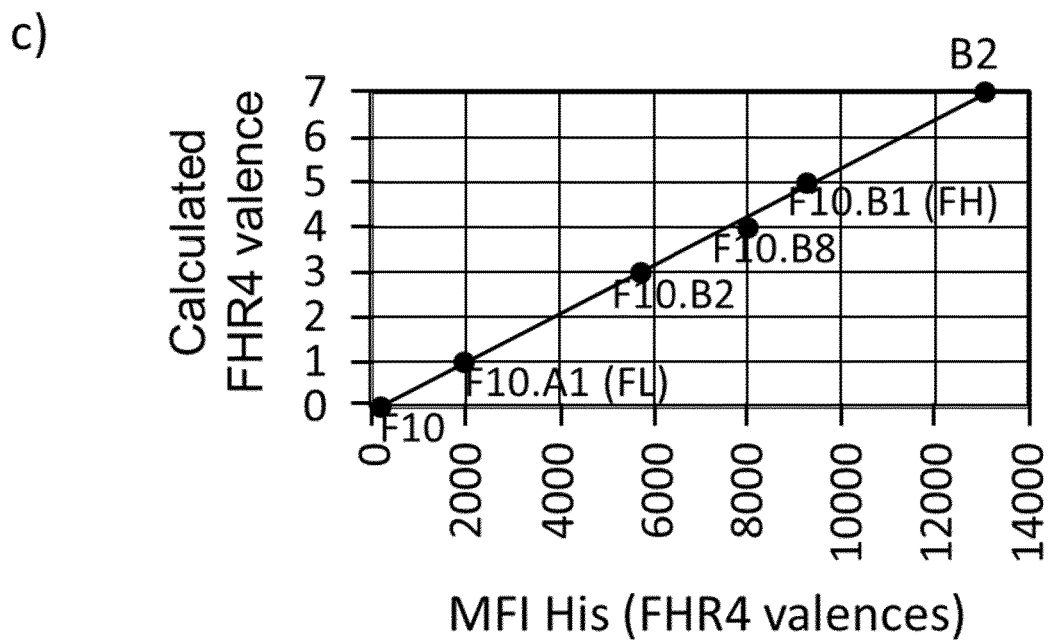

Analysis by Flow Cytometry of the Relationship Between FHR4 Valence within Trifunctional Multimers and CAP-Activation Levels on BT474 Breast Cancer Cells (FIG. 6)

The nomenclature used for the 4 representative trifunctional heteromultimers from lowest-FHR4 to highest-FHR4 valences is FL (F10.A1), F10.B2, F10.B8 and FH (F10.B1). Control multi-2D3 $V_HH$/mono-eGFP bifunctional heteromultimers with FLAG tag is F10, whereas the one expressing the same multimers but with a His tag is B2. The 4 trifunctional heteromultimer-containing crude supernatants expressing various FHR4-valences as well as the 2 control bifunctional heteromultimer-containing crude supernatants with either FLAG or His tags were individually incubated with BT474 cells at saturating concentrations. Multimer-loaded BT474 cells were incubated with veronal buffer and ABO-compatible NHS and analysed by flow cytometry as described previously. F10 represents the Oct-valence, whereas B2 represents the 7α-valences. Trastuzumab anti-Her2 therapeutic monoclonal antibody was used as a negative control for complement activation. Trifunctional heteromultimers display a His tag-representative of the FHR4 effector function—which varies from 1 to 6. The MFI for His, C3b and eGFP were measured. Multimer concentrations in the crude supernatants are in the range of 220 nMoL, which represents a saturating concentration for the amount of BT474 cells used in the present experiment. Statistical analysis: Two-tailed paired t test. Ns:p≥0.05; *: p<0.05; : p<0.01; *: p<0.001.

Figure 7:
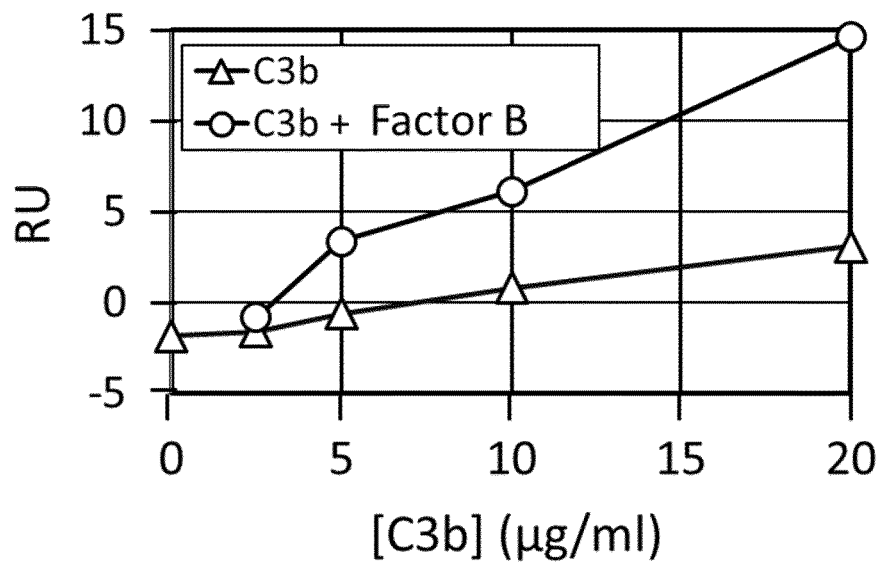

Biacore Analysis of the Binding of C3b and C3bB Complexes on FHR4-Trifunctional Heteromultimers (FIG. 7)

Purified trifunctional high FHR4-valence heteromultimers (FH: multi-FHR4.C4bpα.His/multi-2D3 $V_HH$ anti-Her2.C4bpα.FLAG/mono-eGFP.C4bpβ) and control bifunctional heteromultimers (B2: multi-2D3.$V_HH$ anti-Her2.C4bpα.His/mono-eGFP.C4bpβ) were immobilised onto a carboxymethylated dextran chip via $Ni^{2+}$/NTA chelation on 2 separate channels. Dose-response binding of C3b alone or in the presence of Factor B (about 20 µg/ml) on FH was performed to calculate $K_A$ and $K_D$. After subtraction of the background curves obtained with 0 µg/ml C3b and B2 control bifunctional heteromultimers, specific C3b binding (number of RU) on FH for each C3b concentration is depicted on FIG. 7.

Figure 8:
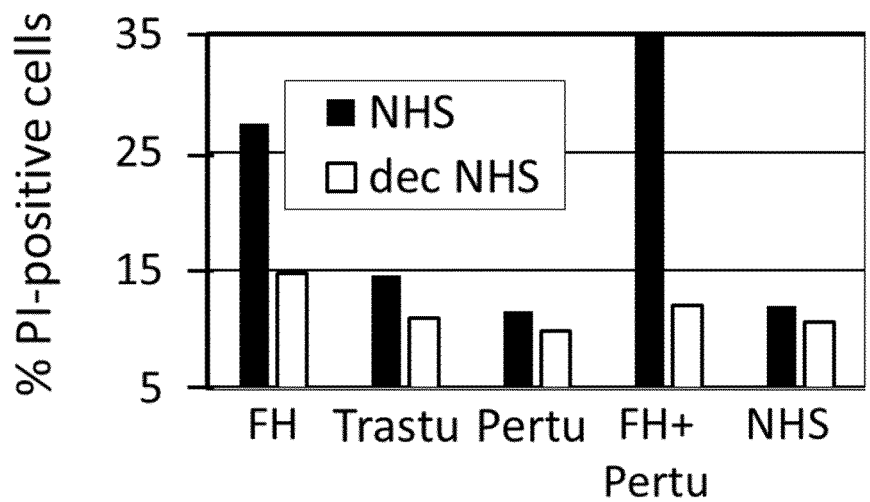

In Vitro Trifunctional Heteromultimer-Mediated Complement-Dependent Cytotoxicity (FIG. 8)

Trifunctional FH multimers were tested in vitro for their ability to elicit CDC on Her2-overexpressing SK-OV-3 target cells. SK-OV-3 tumour cells were incubated with about 200 nMoL of different drugs (FH, Trastuzumab, Pertuzumab, FH+Pertuzumab or no drug), followed by incubation with veronal buffer and NHS. Since 2D3 $V_HH$ anti-Her2 shares the same epitope than Trastuzumab, the combination FH+Trastuzumab has not been included in the present experiment. As negative control for inactive complement, decomplemented NHS was used. Propidium iodide was added just prior to flow cytometry analysis. Percentage of PI-positive (dead) and PI-negative (live) cells was calculated for each condition.

Optimized Heteromultimeric Immunoconjugates Overcome a Complement Inhibitory Threshold to Elicit Strong C3b Deposit on SK-OV-3 Cells (FIG. 9)

Cells expressing high-FHR4 valence trifunctional heteromultimers (multi-FHR4.C4bpα.His/multi-2D3 VHH anti-Her2.C4bpα.FLAG/mono-eGFP.C4bpβ, FIG. 6) were sequentially single-cell sorted to identify a clone expressing optimised trifunctional high-FHR4 valence heteromultimers with highest FHR4 valences (data not shown). Mean FHR4 valence analysed on SK-OV-3 cells analysed by FACS showed a enhancement of a factor x2.32, when compared to initial high-FHR4 valence multimer described in FIG. 6. To confirm the relationship between FHR4 valences and CAP activation, optimised high-FHR4 and low-FHR4 valence multimers were compared (a) for their mean FHR4-valence and (b) for their ability to mediate C3b-deposits on target cells. Two-fold serial dilutions of purified multimers were incubated with SK-OV-3 target cells in the presence of NHS. Cells were then stained with a primary anti-FHR4 or anti-C3b mAb, then a matching secondary Ab and then analysed using flow-cytometry.

FHR4-Multimer-Directed CAP Activation, MAC Formation and Complement-Dependent Cytotoxicity on SK-OV3 Tumor Cells Upon mCRPs Knockdown (FIG. 10)

a) Single (CD46, CD55 or CD59), triple mCRP-knockdown variants and SK-OV-3 wild type (WT) were incubated with optimised high-FHR4 valence multimers in the presence of NHS. Cells were then stained either with an anti-C3b/iC3b (7C12) or antiC5b9 (aE11) mouse mAbs, followed by a secondary Ab APC-conjugated. MFI for C3b or C5b9 corresponding to multimer-mediated C3b deposit and MAC formation were measured and expressed as percentage of the MFI for SK-OV-3 WT cells (FIG. 10a). b) SK-OV-3 variants or WT were incubated with (i) multimers and NHS, (ii) multimers and decomplemented NHS, (iii) NHS alone or (iv) Trastuzumab and NHS. Multimer-mediated CDC was measured using flow cytometry as percentage of PI-positive cells (FIG. 10b).

Flow Cytometry Analysis of Annexin V-PI Staining Showed that Multimer-Directed CDC on SK-OV-3 mCRP-Knockdown Variants is a Necrotic Process (FIG. 11)

FHR4-directed complement-mediated cell death was analysed on SK-OV-3 WT cells incubated with 1) NHS, 2) NHS and 15 µg/ml the purified high-FHR4 valence trifunctional heteromultimers, or 3) decomplemented NHS and multimers. After 10 min or 60 min, the reaction was stopped in ice. Cells were then stained with PI/annexin V (AnV) and analysed by flow cytometry. a) Percentages of cell staining positive for AnV and PI were measured. b) $PI^+/AnV^-$ (upper left quadrant) and $PI^+/AnV^+$ (upper right quadrant) staining representing primary necrotic cells and secondary necrotic/late apoptotic cells, respectively, are depicted at 10 min and 60 min for 3×siRNA variant and SK-OV-3 WT, with NHS or NHS and multimers.

Tetrafunctional Heteromultimers Directed Against HIV-1 Infected Cells

FHR4-multimers expressing the anti-gp120 PGT121-derived scFv are incubated with latently-infected U1 cell line which expresses low gp120 amounts. U1 are at first stimulated with PMA/ionomycin to enhance the HIV-1 expression and therefore gp120 surface expression. Multimer-loaded U1 cells are incubated with 25% NHS and analysed for C3b binding, MAC formation and percentage of PI-positive cells using FACS analysis.

II) Results

Generation of Heteromultimeric Multifunctional Molecules and Identification of Multimers with PRCAP Low and High Valence in Erythrocyte and Cancer Models (FIG. 1 and FIG. 3)

The Applicant hypothesized that a hetero-multivalent form of Properdin and/or FHR4, associated to a multivalent form of an anchoring function (scFv anti-GYPA), and a monovalent eGFP tracking function, could (i) target human erythrocytes or Her2-expressing cancer cells, and (ii) direct efficient activation of the CAP, leading to (iii) the formation of MACs and subsequent, either haemolysis in autologous conditions (erythrocytes and serum are from the same donor) or lysis of cancer cells. The hypothesis of the Applicant stated that the multivalent expression of positive regulators of the CAP (PRCAP) increases selectively and locally the stoichiometry of the PRCAP at the surface of erythrocytes as well as on cancer cells, which could overcome a complement inhibition threshold (CIT) established by the factor H and mCRPs, in contrast with the use of counterpart monovalent fusion molecules. In order to demonstrate the structure-function relationship and the role of the multivalence in the efficacy of directed-complement activation, the Applicant has developed a technology allowing modulating the effector valence number within expressed heteromultimers, using the Applicant's original C4bp-based multimerising system. The original "α-β" configuration consisted of co-expressing a function A fused to the C4bp C-terminal α-chain (C4bpα) and a function B fused to the C4bp c-terminal β-chain (C4bpβ). The secreted bi-functional heteromultimers displayed 7-time the A protein and a single B protein. In the present work, the A function was the anchoring function (scFv anti-GYPA or $V_HH$ anti-Her2), tagged in C-terminal with a FLAG, whereas the B function was eGFP (FIG. 1, Step 1). These bifunctional multi-scFv anti-GYPA/mono-eGFP or multi-$V_HH$ anti-Her2/mono-eGFP heteromultimers are secreted into the supernatants from stable transfected HEK293 cells. Bi-functional heteromultimer-expressing cells were then further transfected with either Properdin or FHR4 effectors both fused to the C4bpα, and tagged in C-terminal with His 8× and with a vector for hygromycin selection (FIG. 1, Step 2A). There are 2 functions (anchoring and effector functions) fused to the C4bpα within trifunctional heteromultimers, but only effector function are linked to His Tag. Since eGFP was always monovalent within the multimers, the ratio MFI HIs/MFI eGFP was representative of the valence number of the effector functions within the multimers. The ratio MFI His/MFI eGFP within tri-/tetrafunctional heteromultimers bound to target cells is stretched from 1 up to 6, corresponding to the lowest and highest ratios, respectively, although the maximum number of α-chains within the multimers is 7, there is at least one scFv anti-GYPA or $V_HH$ anti-Her2 occupying 1 α-chain out of the 7 to allow the multimers binding to erythrocytes or Her2-tumour cells.

Relationship Between PRCAP Valence within Multimers, Opsonisation and Hemolysis Efficacy in the Erythrocyte Target Model (FIG. 4 a, b)

Six purified heteromultimers [trifunctional PL, PH, FL, FH, tetrafunctional CP, bifunctional A heteromultimers lacking FHR4 function (multi-scFv anti-GYPA.C4bpα.His/mono-eGFP.C4bpβ)] used at saturating concentrations have further been tested in vitro for (a) their ability to direct complement activation on human erythrocytes, and (b) to elicit subsequent hemolysis. When comparing FIG. 4 a & b, there is a remarkable correlation between levels of C3b depositions on erythrocytes and percentages of hemolysis. Low-(PL) and high-Properdin (PH) valence trifunctional heteromultimers led to 5.5% and 45% hemolysis, respectively, whereas A negative control led to 5.4% hemolysis. When compared to the A control, PL had no lytic activity, whereas PH led to 45% hemolysis. Low- (FL) & high-FHR4 (FH) valence trifunctional heteromultimers led to 35% and 82.8% hemolysis, respectively. Tetrafunctional High valence properdin/FHR4 tetrafunctional heteromultimers (CP) led to about 10% higher hemolysis (92.7%) than FH.

In parallel, the PH/PL ratio of valence is 6.36 whereas the FH/FL ratio is 2.36. These data unravel the notion a complement inhibitory threshold (CIT) on cell surface to be overcome to lead hemolysis. Overcoming this CIT requires a certain amount of C3b deposition to be reached on target plasma membrane to generate enough C3-convertase, leading then to the formation of enough membrane attack complexes to create irreversible membrane damages. The more PRCAP binding on target plasma membrane, the higher CAP-activation and C3b deposition. PL were unable to reach this CIT even at saturating concentrations. In contrast, saturating erythrocytes with FL had already a substantial hemolytic activity (35% hemolysis), showing the intrinsic CAP-activation efficacy of FHR4 even at low valences. This can be explained by the fact that properdin needs to oligomerise as dimers, trimers or tetramers—the latest being the most effective—to be able to efficiently bind C3b. In contrast, each FHR4 monomer displays 2 C3b binding sites, and FHR4 binds C3b as monomeric entity. Increasing the effector valence number within trifunctional multimers leads to increasing the stoichiometry of effector functions on target plasma membrane surfaces, in order to overcome the CIT.

Factor H-Mediated Dose-Response Inhibition of Opsonisation of FHR4-Loaded Erythrocytes (FIG. 4 c)

The Applicant wanted to check the ability of soluble factor H to inhibit in a dose-response manner the high-FHR4 valence trifunctional heteromultimer-directed CAP-activation on target erythrocytes. $IC_{50}$ was reached around 40 µg/ml factor H (260 nMoL). Saturating C3b depositions starts decaying for concentrations of factor H of about 8 µg/ml (52 nMoL), whereas saturating concentrations of trifunctional high FHR4-valence heteromultimers are about 60 nMoL. The black curve with squares represents the MFI for eGFP, showing the constant densities of trifunctional multimers on erythrocytes. These data show that factor H competes specifically with FHR4 on erythrocytes to down-regulate in a dose-response manner FHR4-mediated complement activation mimicking complement homeostasis in vivo.

Analysis by Flow Cytometry of the Binding of the 2D3 $V_HH$ Anti-Her2/eGFP Bifunctional Heteromultimer on Two Her2-Overexpressing Breast Tumor Cell Lines (FIG. 5)

Relative Her2 densities were compared between BT474, SK-BR-3 and SK-OV-3 Her2-overexpressing tumour cell lines, using the therapeutic humanised Trastuzumab mAb. FIG. 5 a shows the MFI for anti-Her2 measured by flow cytometry. SK-OV-3 cells express the highest Her2 densities, followed by BT474 and SK-BR-3 cells. Control HEK293 cells do not express Her2. SK-OV-3 express 1.32 time more Her2 than BT474 cells, and 2.1 time more Her2 than SK-BR-3. FIG. 5 b shows the dose-response binding of 2D3 bifunctional multi-$V_HH$ anti-Her2/mono-eGFP heteromultimers on the Her2-expressing cells vs. HEK293 control cells. For the undiluted supernatant, MFI for eGFP are 1236, 772, 516 and 72 for SK-OV-3, BT474, SK-BR-3 and HEK293, respectively. The multimers bind with 1.6 higher densities on SK-OV-3 than on BT474 cells, and 2.4 higher densities on SK-OV-3 than on SK-BR-3 cells, respectively. These differences are related to the differences of Her2 densities previously measured using Trastuzumab. When using undiluted multimer-containing supernatants, bifunctional multimer concentrations are almost at saturating concentrations on SK-BR-3 and BT474 cells, reaching a plateau. In contrast, the multimers do not saturate on SK-OV-3 cells.

This experiment shows that binding of 2D3 bifunctional multi-$V_HH$ anti-Her2/mono-eGFP heteromultimers is specific to HER-2 overexpressed on tumour cells, and the levels of accumulation depend on Her2-densities on these cells.

Flow Cytometry Analysis of the Relationship Between FHR4 Valence within Trifunctional Multimers and C3b Activation Levels on BT474 Breast Cancer Cells (FIG. 6)

FIG. 6 a & b show that, as in the erythrocyte model, there is, in the Her2 tumour model, a remarkable structure-function relationship between FHR4 valences within trifunctional heteromultimers and their ability to active CAP in vitro on Her2-expressing target tumour cells:

Measured MFI for His (MFI/His)—representative of FHR4 valences on BT474 cells—were 1947 and 9246 for the trifunctional heteromultimers with lowest-FHR4 valence (FL) and highest-FHR4 valence (FH), respectively. The FH/FL ratio for MFI/His is 4.75.

Measured MFI for C3b deposition (MFI/C3b) were 234 and 1303 for FL and FH, respectively. The FH/FL ratio for MFI/C3b is 5.57.

MFI/C3b for the control multi-2D3 $V_HH$/mono-eGFP bifunctional heteromultimers was 120. When compared to the control, FL elicited a weak CAP-activation (MFI/C3b 234 vs. 120). However, this weak FL-mediated CAP-activation indicates that FL activity yet slightly overcomes CIT on BT474 cells, like it did in the erythrocyte model.

FHR4-valence number were then calculated. Bifunctional multi-$V_HH$ anti-Her2/mono-eGFP heteromultimers were generated either with a His or a FLAG tag. At saturating concentrations on BT474 cells, measured MFI/His for these bifunctional multimers with His and FLAG Tags allowed establishing a calibration curve where the first point represents the highest His valence (7x), whereas the second point represents the lowest His valence (Ox). The values of MFI/His are on the X-axis, while FHR4 valences are on the Y-axis. The FHR4 valences for the clones FL, F10.B2, F10.B8 and FH are 1, 3, 4 and 5 FHR4 valences, respectively.

To further analyse whether CAP activation is proportional to FHR4 valence increase, ratios MFI His/C3b were calculated for all 4 clones: FL=8.32, F10.B2=10.65, F10.B8=11.56 and FH=7.1, and then ratios for the 2 lowest-FHR4 clones (F10.B2/FL) were divided, as well as ratios for the 2 highest-FHR4 clones (FH/F10.B8). The coefficient for the low-FHR4 valence is 1.28, whereas the coefficient for the high-FHR4 valence is 0.61. These results indicate that CAP-activation—once multimer-mediated CIT has been overcome—takes place as a biphasic phenomenon: The first phase, just above the CIT, requires high FHR4-increase for a low C3b activation. The second phase takes place once CAP-activation in the first phase is initiated. From that point, lower FHR4-increase elicits stronger CAP-activation. This second phase corresponds to an exponential CAP-activation.

To conclude, in the present tumour model, our innovative technology of designing trifunctional heteromultimers with the possibility to modulate PRCAP effector function valences within expressed multimers with respect to the anchoring moiety allowed unraveling the notion of complement inhibitory threshold (CIT). This CIT is established by the presence of membrane-associated complement inhibitory proteins (mCRPs) that are generally overexpressed on tumour cell surfaces, offered a reinforced protection from host complement activation. The CIT also depends on soluble factors such as factor H and C4bp. To overcome the CIT, the key technology is (i) the expression of PRCAP (ii) under multivalent form, (iii) associated to an anchoring moiety, (iv) allowing increasing locally the stoichiometry of PRCAP through progressive accumulation of the multimers on target tumours, to finally elicit efficient CAP-activation by overwhelming mCRPs through excessive activation of the CAP and displace the complement homeostasis towards activation.

Biacore Analysis of the Binding of C3b and C3bB Complexes on Trifunctional High FHR4-Valence Heteromultimers (FIG. 7)

The specificity of binding of C3b to purified trifunctional high FHR4-valence heteromultimers (FH) was investigated using Surface Plasmon Resonance technology (Biacore). As negative control, purified bifunctional 2D3 multi-$V_HH$ anti-Her2/mono-eGFP heteromultimers (B2) lacking FHR4 function were used in parallel and did not show any binding with C3b (data not shown). In contrast C3b dose-response binding was observed on B1.2E3. The number of RU bound after subtraction of the background was 3.08 at 20 μg/ml C3b as shown in the FIG. 7. In the presence of factor B (about 20 μg/ml), the amount of bound C3b was increased to 14.6 RU, showing an enhancement factor of 5. Association ($K_A$) and dissociation ($K_D$) rate constants for the binding of C3b to FHR4 in absence or in the presence of factor B were then determined from the dose-responses curves and are depicted in Table 1. These data show the strong affinity of C3b for trifunctional high FHR4-valence heteromultimers for C3b. The presence of factor B increased of about 2 logs the binding affinity of C3b to FHR4, showing the stabilisation of C3b by FB through the formation of C3bB complexes as observed in physiological conditions.

TABLE 1

Association ($K_A$) and dissociation ($K_D$) rate constants for the binding of C3b to FHR4
Binding of C3b to trifunctional FHR4 multimers

|  | $K_A$ (1/M) | $K_D$ (M) |
| --- | --- | --- |
| C3b | $1,05.10^{+6}$ | $9,52.10^{-7}$ |
| C3b + FB | $1,14.10^{+8}$ | $8,73.10^{-9}$ |

Table1: Association ($K_A$) and dissociation ($K_D$) rate constants for the binding of C3b to the trifunctional high - FHR4 valence heteromultimers In Vitro Trifunctional Heteromultimer-Mediated Direct CDC (FIG. 8)

FIG. 8 depicts direct FH-mediated CDC. After deduction of the background obtained in the presence of decomplemented NHS, FH led to 12.7% and 23% PI-positive cells alone, or in combination with Pertuzumab, respectively. Antibody-mediated CDC is 3.7% and 1.7% for Trastuzumab and Pertuzumab, respectively. The cooperative effect when combining 2E9 and Pertuzumab indicates the possibility of combining the lead immuno-conjugates with other drugs to enhance the CDC efficacy.

The principal effector functions of the complement system in innate immunity are to promote phagocytosis of complement-opsonised pathogenic microorganisms, as well as senescent or apoptotic cells, to stimulate inflammation, and to induce their lysis. Complement activation on opsonised microorganisms leads to the generation of C3b that can be degraded into iC3b and further into C3d, g and C3d. C3b and degradations products bind complements receptors (CR1, CR3 and CR4) on neutrophils and macrophages. This mechanism is called complement-dependent cell-mediated cytotoxicity or CDCC. NK-mediated cell killing can also take place through CDCC. In contrast, CDC leading to direct cytolysis is not the principal mechanism of destruction of complement-opsonised cells, in particular tumour cells, the real therapeutic efficacy of drugs directing the activation of the CAP such as multifunctional heteromultimeric protein complexes towards tumour targets needs to be tested in vivo where CDC and CDCC can occur concomitantly. NUDE mice model is a convenient in vivo model since subcutaneous human tumour xenografts can be developed, and NUDE mice have a fully functional complement system as well as functional NK, macrophages and neutrophils.

Optimized Heteromultimeric Immunoconjugates Overcome a Complement Inhibitory Threshold to Elicit Strong C3b Deposit on SK-OV-3 Cells (FIG. 9)

At similar saturating concentrations of each multimer, FHR4 densities were 5 times higher on SK-OV-3 cells (expressing the highest level of mCRPs among the tested HER-2 expressing cells, FIG. 5) for the optimized high-FHR4 valence multimers isolated after single cell sortings than for the low-FHR4 valence multimers (clone F10.A1) (72953 vs 14487 MFI, respectively) (FIG. 9a), whereas C3b activation was 7 times higher for optimized high-FHR4 valence than for low-FHR4 valence multimers (37541 vs 5432 MFI, respectively) (FIG. 9b). From a concentration of 0.8 µg/ml (corresponding to a MFI for FHR4 of 26496), optimised high FHR4-valence multimer starts triggering CAP-activation on SK-OV-3 cells (FIG. 9b) by efficiently competing with soluble factor H, allowing engaging C3b amplification loop on target cells (bold dotted line on FIG. 9), thus overcoming the Complement Inhibitory Threshold (CIT). In contrast, low-FHR4 valence multimers could not overcome CIT and did not elicit efficient CAP activation, even at saturating concentrations (up to 30 µg/ml). Detailed analysis of FIGS. 9a & 9b indicates that CAP activation on SK-OV-3 target cells takes place as a bimodal reaction. During an initial phase, progressive increase of FHR4 densities does not activate CAP, until CIT is reached. Once CIT is overcome, further increase of FHR4 density on cells triggers CAP activation and subsequent C3b deposit. This bimodal phenomenon shows the importance of FHR4 multimerisation to achieve high local FHR4 densities on target membrane to reach the critical point of phase switch on cell surface. From this point, linear FHR4 increase suddenly modifies FHR4/factor H balance that favours the formation of FHR4-C3b complexes to the detriment of the initial factor H-C3b complex formation. In contrast to factor H-C3b complexes that lead to inactivation of C3b, FHR4-C3b complexes further allow functional C3-convertase assembly. Optimized high-FHR4 valence multimers thus dramatically enhanced the ability of FHR4 to compete with factor H, which is consistent with a potential use as therapeutics, since natural FHR4 binding affinity for C3b on C3b-opsonised cell surfaces is weaker than Factor H and furthermore FHR4 is unable to form dimers on opsonised cell surfaces in physiological conditions.

FHR4-Multimer-Directed CAP Activation, MAC Formation and Complement-Dependent Cytotoxicity on SK-OV3 Tumor Cells Upon mCRPs Knockdown (FIG. 10)

We observed a variability of mCRP expression on SK-OV-3 cells leading to a variability of multimer-induced complement-mediated CDC. We next generated stable single (CD46, CD55 or CD59) as well as triple mCRP-knockdown SK-OV-3 variants using siRNA-induced silencing of mCRP expression. These mCRP-depleted variants allow investigating the role of mCRPs in CAP activation efficacy via C3b deposit, the subsequent amounts of MAC formed (C5b9 staining) and the resulting complement-dependent cytotoxicity.

Single mCRP-knockdown variants display increased multimer-mediated C3b deposit as well as MAC formation around a factor 2, when compared to SK-OV-3 WT (FIG. 10a). Triple mCRP-knockdown variant displayed a similar 2 fold increase of C3b deposit but MAC formation was remarkably increased of a factor of 5.5, when compared to SK-OV-3 WT cells (FIG. 10a) further triggering increased CDC, leading to 58% PI-positive cells (FIG. 10b). These results indicate that optimised high-FHR4 valence multimers are capable of triggering the initial C3b deposits on target cells, whatever mCRP expression, by efficiently competing with soluble factor H for C3b binding. With that regards, optimised high-FHR4 valence multimers do successfully overcome complement inhibitory threshold (CIT) on target surface. However, overexpressed mCRP further inhibit amounts of C3b deposit (CD46/CD55), MAC formation efficacy (CD59) and subsequent CDC.

Flow Cytometry Analysis of Annexin V-PI Staining Showed that Multimer-Directed CDC on SK-OV-3 mCRP-Knockdown Variants is a Necrotic Process (FIG. 11)

At 10 and 60 min. of multimer-mediated complement activation, percentage of $PI^+/AnnV^+$ double positive staining was 26.3% and 42.6% for the triple mCRP-knockdown SK-OV-3 variant, respectively (FIG. 11a), whereas the SK-OV-3 WT, displayed 2% and 2.73% $PI^+/AnnV^+$ double positive staining at 10 and 60 min., respectively. During the course of multimer-mediated CAP-activation, early apoptotic cells ($PI^-/AnnV^+$) were observed neither in SK-OV-3 variants nor in SK-OV-3 WT (FIG. 10b), indicating the absence of externalization of mitochondrial phosphatidylserines, which is the earliest feature of apoptosis triggering. These results indicate that multimer-mediated CDC in triple mCRP-knockdown SK-OV-3 variant undergo cell death through a necrotic process, leading to a sequential shifts from $PI^-/AnnV^-$ to $PI^+/AnnV^-$ stainings (primary necrotic), then from $PI^+/AnnV^-$ to $PI^+/AnnV^+$ double positive stainings (secondary necrotic with heavy damage to cell membranes). These results are consistant with cell necrosis which is generally associated to extreme conditions (e.g. complement attack) where cells die through massive unregulated processes of rapid disruption of their plasma membrane that collapses and cytoplasmic structures and cells are rapidly lysed.

Tetrafunctional Heteromultimers Directed Against HIV-1 Infected Cells

PMA/ionomycin-stimulated U1 cells express gp120. Moreover, they do not overexpress mCRPs like tumour cells. We observe multimer-directed CAP activation and subsequent C3b deposits, lytic levels of MAC formation leading to subsequent CDC.

Using decomplemented NHS, C3b deposition is abrogated, neither MAC formation is observed, nor CDC.

Example 2

I) Material & Methods

For cells and reagents used in Example 2, see cells and reagents of Example 1. mCRP-knockdown SK-OV-3 variants were established in house using commercially available Sigma-Aldrich pLK-O1 plasmids expressing shRNA for CD46 (NM_002389), CD55 (NM_000574), CD59 (NM_000611).

Strategy to Generate High FHR4-Valence Trifunctional Heteromultimers with Concomitant CDC and ADCC Activities (FIG. 12)

CAP-effector function (EF) and targeting function (TaF) are cloned in the cassette for EF or TaF functions shown in FIG. 2a. The cassette has been modified as followed: HIS or FLAG tags (T) downstream from the C4bp C-terminal α-chain multimerising scaffold (MS) have been removed and replaced by the hinge, CH2 and CH3 domains of IgG. This new cassette can also be cloned in the bicistronic vector shown in FIG. 2c, downstream from promoter 1, instead of TaF cassette. The strategy to generate trifunctional heteromultimers remains the same. In step 1, the targeting and tracking functions are cotransfected. After clonal selection, selected cell clone expressing high amounts of bifunctional heteromultimers is further transfected with the CAP-effector cassette (EFF) (step 2) and a plasmid for a second antibiotic selection. Screening for high FHR4-valence multimers is performed by incubating target cells with the multimer-containing supernatants, a staining with an anti-FHR4 mAb, and flow cytometry analysis. Ratio MFI for FHR4/MFI eGFP are measured.

Adding Fc from IgG as a Functional Moiety Allowed Multimer-Mediated ADCC (FIG. 13)

To generate heteromultimers with ADCC activity, a Fc function for ADCC was fused downstream from the C4bp C-terminal α-chain scaffold for multimerisation together with the V$_H$H anti-HER-2 targeting function (FIG. 13a). The V$_H$H anti-Her2.C4bpα.Fc/eGFP.C4bpβ bifunctional heteromultimer is called "Fc" (cf. FIGS. 12, 13 a). As negative control, CH2 domain was omitted. Control bifunctional heteromultimers are called "Fc(CH3)". Bifunctional V$_H$H anti-Her2.C4bpα.Fc/eGFP.C4bpβ multimers (FIG. 13, step 1) as well as control multimers were tested using NK92-humCD16 effector cells line and SK-OV-3 target cells. SK-OV-3 were at first incubated with 5-fold serial dilutions of multimers (2, 0.4 and 0.08 µg/ml), then incubated in the presence of NK92 NK92-humCD16 (ratio E:T/5:1). Trastuzumab and pertuzumab were used as positive controls instead of the multimers at same serial dilutions. CD107 (a) and IFNg (b) expressions of NK92 cells were analysed using flow cytometry.

II) Results

Strategy to Generate High FHR4-Valence Trifunctional Heteromultimers with Concomitant CDC and ADCC Activities (FIG. 12)

The Fc is added downstream from C4bp C-terminal α-chain multimerising scaffold for both CAP-effector and targeting functions. The number of Fc is thus constant, fixed at seven valences, irrespective of the ratio EFF/TaR. Our preliminary results obtained with the bifunctional heteromultimers showed in FIG. 13 indicate that the monomeric Fc fragments are able to dimerise, theoretically leading to up to 3 Fc dimers and one Fc monomer. It has been shown that different oligomeric forms of human IgG1 could enhance the binding to FcγRs and C1q through their increased avidity (8). Our ADCC results show that NK cells are activated (expression of CD107 and IFNγ) by the SK-OV-3-bound multimers displaying the whole Fc (Hinge-CH2-CH3), but not when multimers display the Fc(CH3). This is due to the presence of Fc(CH2) fragment that is responsible for the Fc-dimerisation as well as for the binding of the Fc to FcγRIIIA on NK92-humCD16 cells. At higher concentration (0.4 to 2 µg/ml), antibody- and Fc multimer-mediated ADCC of NK92-humCD16 are in the same range. In contrast, at lower concentration (0.08 µg/ml), ADCC is stronger with the Fc multimer than with therapeutic antibodies: percentage of CD107-positive cells is 1.5× higher with the Fc multimers, whereas percentage of IFNγ-positive cells is about 4.5-5× higher with the Fc multimers, when compared to the therapeutic antibodies. This may be explained by the presence of multiple Fc dimers within Fc multimers that are able to bind with higher affinity to CD16 than conventional IgGs. As a consequence, at lower multimer concentration, ADCC is better sustain than when using therapeutic antibodies.

Adding Fc from IgG as a Functional Moiety Allowed Multimer-Mediated ADCC (FIG. 13)

FIGS. 13a and 13b showed clear evidence of multimer-mediated ADCC, leading to CD107 expression on NK92 cells (FIG. 13a) as well as IFNγ production. Comparison with therapeutic antibodies showed that Fc multimeric V$_H$H anti-Her2 immunoconjugates elicited CD107 expression and IFNγ production in NK92 effector cells that was at least as good as Trastuzumab, and higher than both therapeutic antibodies at lower drug concentrations (80 ng/ml). These important data suggest that the addition of the Fc from IgG downstream from the C4bp C-terminal α-chain scaffold fragment allows Fc monomers within a single multimeric molecule to dimerise as in native IgG, whereby Fc dimers (up to 3 for a single multimer) elicit efficient ADCC activity.

The negative control multimer lacking CH2-domain strongly involved in the Fc dimer formation—confirms the effective Fc dimeric association of within V$_H$H anti-Her2-C4bpα-Fc multimers.

REFERENCES

1. Vuagnat, B. B., J. Mach, and J. M. Le Doussal. 2000. Activation of the alternative pathway of human complement by autologous cells expressing transmembrane recombinant properdin. *Molecular immunology* 37: 467-478.
2. Spitzer, D., L. M. Mitchell, J. P. Atkinson, and D. E. Hourcade. 2007. Properdin can initiate complement activation by binding specific target surfaces and providing a platform for de novo convertase assembly. *Journal of immunology* 179: 2600-2608.
3. Libyh, M. T., D. Goossens, S. Oudin, N. Gupta, X. Dervillez, G. Juszczak, P. Cornillet, F. Bougy, B. Reveil, F. Philbert, T. Tabary, D. Klatzmann, P. Rouger, and J. H. Cohen. 1997. A recombinant human scFv anti-Rh(D) antibody with multiple valences using a C-terminal fragment of C4-binding protein. *Blood* 90: 3978-3983.
4. Hebecker, M., and M. Jozsi. 2012. Factor H-related protein 4 activates complement by serving as a platform for the assembly of alternative pathway C3 convertase via its interaction with C3b protein. *The Journal of biological chemistry* 287: 19528-19536.
5. Anstee, D. J., and P. A. Edwards. 1982. Monoclonal antibodies to human erythrocytes. *European journal of immunology* 12: 228-232.
6. Klingemann, H., L. Boissel, and F. Toneguzzo. 2016. Natural Killer Cells for Immunotherapy—Advantages of the NK-92 Cell Line over Blood NK Cells. *Frontiers in immunology* 7: 91.
7. Iwaki, D., Kanno, K., Takahashi, M., Endo, Y., Matsushita, M., Fujita, T. 2011.
The role of mannose-binding lectin-associated serine protease-3 in activation of the alternative complement pathway. *J. Immunol.* 187(7):3751-8.
8. Diebolder, C. A., F. J. Beurskens, R. N. de Jong, R. I. Koning, K. Strumane, M. A. Lindorfer, M. Voorhorst, D. Ugurlar, S. Rosati, A. J. Heck, J. G. van de Winkel, I. A. Wilson, A. J. Koster, R. P. Taylor, E. O. Saphire, D. R. Burton, J. Schuurman, P. Gros, and P. W. Parren. 2014. Complement is activated by IgG hexamers assembled at the cell surface. *Science* 343: 1260-1263.
9. Klein, M., N. Haeffner-Cavaillon, D. E. Isenman, C. Rivat, M. A. Navia, D. R. Davies, and K. J. Dorrington. 1981. Expression of biological effector functions by immunoglobulin G molecules lacking the hinge region. *Proceedings of the National Academy of Sciences of the United States of America* 78: 524-528.

The invention claimed is:

1. A multifunctional heteromultimeric protein complex for directing complement-dependent cytolysis and/or antibody-dependent cell-mediated cytotoxicity (ADCC), comprising three or more different functional components present in a defined relative ratio, wherein the three or more different functional components are each independently selected from a tracking component, a targeting component and an effector component;

wherein said tracking component is selected from fluorescent dyes, magnetic beads, biotin for staining with labelled avidin or streptavidin conjugate, enzymes, substrates, cofactors, chemiluminescent groups, chromogenic agents, colorimetric labels and beads;

wherein said targeting component allows binding of the multifunctional heteromultimeric protein complex to a target cell and is selected from antibodies, binding fragments thereof, ligands to a target cell receptor and soluble receptors;

wherein said effector component comprises a factor selected from factor H-related protein 4 (FHR4), Properdin, MBL-associated-serine-protease 3 (MASP-3), P-selectin and monomeric Fc;

wherein said multifunctional heteromultimeric protein complex comprises eight multimerizing scaffold polypeptides, of which seven are a C-terminal part of an alpha-chain of a C4b binding protein (C4bp) multimer and one is a C-terminal part of a beta-chain of a C4bp multimer;

wherein each of said seven C-terminal parts of the alpha-chain of the C4bp multimer is fused to two functional components and one of said two functional components is located upstream and the other functional component is located downstream of said C-terminal part of the alpha-chain of the C4bp multimer; and wherein said C-terminal part of the beta-chain of the C4bp multimer is fused to a tracking component.

2. The multifunctional heteromultimeric protein complex according to claim 1, comprising at least two monomeric Fc.

3. The multifunctional heteromultimeric protein complex according to claim 1, comprising at least three factor H-related protein 4 (FHR4) proteins.

4. The multifunctional heteromultimeric protein complex according to claim 1, wherein one of the functional components fused to the C-terminal part of the alpha-chain of the C4bp multimer is monomeric Fc.

5. The multifunctional heteromultimeric protein complex according to claim 4, wherein the monomeric Fc component is monomeric Fc of IgG comprising the hinge and the CH2 and CH3 domains of IgG.

6. The multifunctional heteromultimeric protein complex according to claim 1, comprising at least three Fc dimers.

7. The multifunctional heteromultimeric protein complex according to claim 1 wherein at least one of the targeting components is an antibody directed against a tumor antigen, against a surface marker of erythrocytes or against a pathogen-associated surface marker.

8. The multifunctional heteromultimeric protein complex according to claim 1 wherein at least one of the targeting components is an antibody or fragment thereof directed against tumor-associated antigen HER2/neu or scFv anti-GYPA.

9. The multifunctional heteromultimeric protein complex according to claim 1, comprising seven C-terminal parts of the alpha-chain of the C4bp multimer fused to a targeting component, wherein the targeting component is an antibody directed against a tumor antigen, against a surface marker of erythrocytes or against a pathogen-associated surface marker; and monomeric Fc;

wherein the targeting component is located upstream of the C-terminal part of the alpha-chain of the C4bp multimer and monomeric Fc is located downstream of the C-terminal part of the alpha-chain of the C4bp multimer.

10. The multifunctional heteromultimeric protein complex according to claim 1, wherein the tracking component is a tag and a proteolytic cleavage site is present between the tag and the C-terminal part of the beta-chain of the C4bp multimer.

11. The multifunctional heteromultimeric protein complex according to claim 1, wherein the functional component located upstream of said C-terminal part of the alpha-chain of the C4bp multimer is a targeting component or an effector component and wherein the functional component located downstream of said C-terminal part of the alpha-chain of the C4bp multimer is an effector component.

* * * * *